(12) United States Patent
Ryan et al.

(10) Patent No.: US 6,462,809 B1
(45) Date of Patent: Oct. 8, 2002

(54) REFRACTOMER AND METHOD FOR QUALITATIVE AND QUANTITATIVE MEASUREMENTS

(75) Inventors: Thomas E. Ryan, Batavia; Michael J. Byrne, East Aurora, both of NY (US)

(73) Assignee: Leica Microsystems, Inc., Buffalo, NY (US)

(*) Notice: Subject to any disclaimer, the term of this patent is extended or adjusted under 35 U.S.C. 154(b) by 0 days.

(21) Appl. No.: 09/439,876

(22) Filed: Nov. 12, 1999

Related U.S. Application Data

(60) Provisional application No. 60/142,207, filed on Jul. 2, 1999, and provisional application No. 60/108,414, filed on Nov. 13, 1998.

(51) Int. Cl.[7] .............................................. G01N 21/41
(52) U.S. Cl. ...................................... 356/128; 356/136
(58) Field of Search ................................. 356/128, 135, 356/136, 445; 385/12, 129, 130, 131

(56) References Cited

U.S. PATENT DOCUMENTS

| | | | |
|---|---|---|---|
| 3,612,696 A | 10/1971 | Broerman | 356/128 |
| 3,778,165 A | 12/1973 | Grubb et al. | 356/128 |
| 4,286,873 A | 9/1981 | Carson | 356/130 |
| 4,381,895 A | 5/1983 | Hughes et al. | 356/134 |
| 4,640,616 A | 2/1987 | Michalik | 356/136 |
| 4,844,869 A | 7/1989 | Glass | 422/68 |
| 4,909,990 A | 3/1990 | Block et al. | 422/82.11 |
| 5,071,248 A | 12/1991 | Tiedenthaler et al. | 356/128 |
| 5,164,589 A | 11/1992 | Sjodin | 250/227.24 |
| 5,300,423 A | 4/1994 | Zoha et al. | 435/7.1 |
| 5,304,465 A | 4/1994 | Garland et al. | 435/4 |
| 5,313,264 A | 5/1994 | Ivarsson et al. | 356/73 |
| 5,341,215 A | 8/1994 | Seher | 356/445 |
| 5,344,784 A | 9/1994 | Attridge | 436/518 |
| 5,377,008 A | 12/1994 | Ridgway et al. | 356/361 |
| 5,415,842 A | 5/1995 | Maule | 422/82.05 |
| 5,422,714 A | 6/1995 | Fladd | 356/128 |
| 5,434,663 A | 7/1995 | Maule | 356/300 |
| 5,478,755 A | 12/1995 | Attridge et al. | 436/518 |
| 5,479,260 A | 12/1995 | Fattinger | 356/361 |
| 5,496,701 A | 3/1996 | Pollard-Knight | 435/7.4 |
| 5,538,850 A | 7/1996 | King et al. | 435/6 |
| 5,563,707 A | 10/1996 | Prass et al. | 356/361 |
| 5,631,171 A | 5/1997 | Sandstrom et al. | 436/518 |
| 5,633,724 A | 5/1997 | King et al. | 356/445 |

(List continued on next page.)

FOREIGN PATENT DOCUMENTS

EP 0836092 4/1998 ............ G01N/21/55

*Primary Examiner*—Frank G. Font
*Assistant Examiner*—Michael P. Stafira
(74) *Attorney, Agent, or Firm*—Maria M. Eliseeva, Esq.; Brown Rudnick Berlack Israels, LLP

(57) ABSTRACT

A sensor apparatus and associated method for sensing and monitoring specific binding of analyte to an immobilized binding layer are disclosed. The apparatus preferably comprises an automatic critical angle refractometer having a linear scanned array and an optical system for illuminating a portion of the array, which illumination depends upon the refractive index of the binding layer deposited on an optically transparent element. The apparatus further includes a flow cell for bringing the analyte in contact with the binding layer. The apparatus also includes a computer for receiving and processing refractive index data from the critical angle refractometer during the reaction between the analyte and the layer, which computer may be peripherally connected to the refractometer or enclosed within the refractometer housing. A preferred sensing method of the present invention generally comprises providing a critical angle refractometer generating light impinging upon the immobilized binding layer, contacting the binding layer with a contacting phase, measuring the critical angle of total reflection, which measurements are indicative of the presence or absence of interactions between the analyte and the binding layer.

30 Claims, 27 Drawing Sheets

U.S. PATENT DOCUMENTS

| | | | |
|---|---|---|---|
| 5,639,668 A | 6/1997 | Neel et al. | 436/172 |
| 5,640,234 A | 6/1997 | Roth et al. | 356/128 |
| 5,641,640 A | 6/1997 | Hanning | 435/7.92 |
| 5,663,790 A | 9/1997 | Ekstrom et al. | 356/128 |
| 5,680,209 A | 10/1997 | Machler | 356/319 |
| 5,694,930 A | 12/1997 | Pries et al. | 128/633 |
| 5,712,705 A | 1/1998 | Fattinger et al. | 356/354 |
| 5,815,278 A | 9/1998 | Johnston et al. | 356/445 |
| 5,822,073 A | 10/1998 | Yee et al. | 356/445 |
| 5,854,863 A | 12/1998 | Erb et al. | 385/12 |
| 5,923,031 A | 7/1999 | Naya | 250/227.25 |

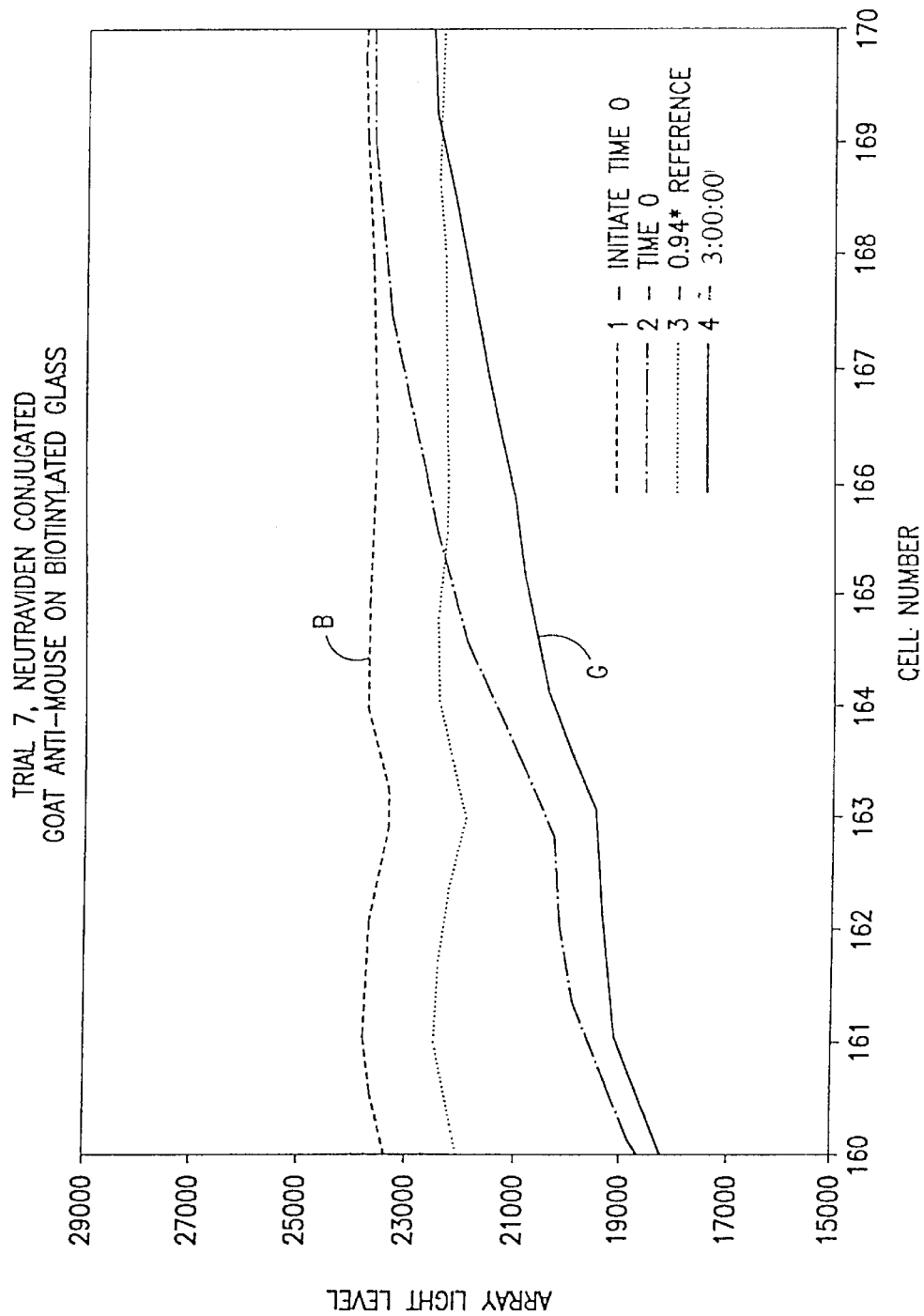

REFRACTOMER AND METHOD FOR QUALITATIVE AND QUANTITATIVE MEASUREMENTS

CROSS-REFERENCE TO RELATED APPLICATIONS

This application claims priority on earlier filed U.S. provisional patent application Ser. No. 60/108,414, filed Nov. 13, 1998, and U.S. provisional patent application Ser. No. 60/142,207, filed Jul. 2, 1999, which are incorporated herein by reference.

FIELD OF THE INVENTION

The present invention relates generally to the field of refractive index based sensing devices. More particularly, the invention relates to a critical angle refractometer and method for sensing and monitoring interactions between an analyte and a binding layer.

BACKGROUND OF THE INVENTION

Analysis of qualitative and quantitative aspects of interactions between analytes and various types of binding layers is important to a wide range of scientific and industrial applications. Consequently, sensors which monitor specific binding of a sample analyte to a particular type of ligands immobilized on the sensing surface have been developed. The term "ligands" here means a type of molecules exhibiting specific binding affinity to another type of molecules. The terms "immobilized binding layer", "binding layer", or "sensing layer" here mean a layer formed by ligands immobilized on a sensing surface. The term "sensing surface" means an interface between two media, one of which is the binding layer. The term "contacting phase" here means a fluid phase, which is brought in contact with the binding layer. The term "analyte", or "sample analyte", here means the ligands contained in the contacting phase. An analyte in a contacting phase may or may not possess binding affinity to a particular binding layer.

For example, sensors based on the surface plasmon resonance (SPR) phenomenon are known to detect and measure changes in the refractive index of a sample analyte contacting a sensing layer. SPR sensors are often used in such applications as investigation of surface and interface effects, spectroscopy, differential reflectivity, immunoasays. SPR sensors are based on the following principle: when a thin metal layer is illuminated by an incident beam of light, under certain circumstances the energy of the light beam can excite free electrons on the illuminated surface of the metallic film. In particular, the beam will resonate with the surface electrons, which resonance will lead to the creation of an electrical field extending within the range of about 200 nanometers. The resonance occurs at a certain angle of incidence of the incoming light beam and depends on the refractive index of a substance located within the range affected by the generated electrical field. Binding or dissociation of the analyte and an immobilized binding layer at the sensor surface changes the local refractive index at the surface and produces a shift in the resonant angle of incidence, which has been shown to be proportional to the concentration of ligands bonded to an immobilized binding layer up to a predetermined limiting concentration. Thus, by electro-optically monitoring changes of the refractive index at the sensing surface using SPR, qualitative sensing of ligands and quantitative characterization of various binding kinetics and equilibria are possible.

An example of an SPR biosensor is schematically illustrated in FIG. 1. SPR biosensor 2 includes a prism 4 having a test surface thereof coated by a thin metallic film 6. A first type of ligands 8 is immobilized on metallic film 6, and an analyte 10 is introduced into the contacting phase above the test surface. A light source 12 of predetermined wavelength directs an incident beam 14 to metallic film 6, and a photosensitive detector 16 is arranged to monitor the intensity of reflected beam 14'. At a certain angle of incidence $\alpha$ of beam 14, resonant excitation of electrons (surface plasmons) in metallic film 6 results in absorption of incident beam 14 and, consequently, in an energy loss in the reflected beam 14', which is observed experimentally as a sharp minimum in the intensity of light received by detector 16, as illustrated in FIG. 2.

While SPR sensors exhibit a high degree of sensitivity to changes in refractive indices, which makes them a useful research tool, immobilizing a binding layer on a metallic layer is both difficult and limiting. It is difficult, because the immobilization technique must attach the ligands in a native conformation and in a uniformly reactive and accessible orientation, to a metallic surface that does not allow for a significant amount of non-specific binding. A number of various immobilization techniques have been described in the art, with the choice of a technique being dependent upon particular ligands involved. Because of these and other difficulties associated with manufacturing SPR sensors, such sensors are expensive. Therefore, it would be desirable to come up with a less expensive device capable of measuring changes of the refractive indices caused by interactions between various ligands.

An example of a suitable device for sensitive and quantitative measurements associated with changes in refractive indices is a critical angle refractometer. The operation of a critical angle refractometer is based on the following principle. When light is incident on a surface separating two media, the light is refracted at the interface between the two media in accordance with Snell's law:

$$n \sin I = n' \sin I'$$

where n and n' are the refractive indices of the two media, and I and I' are the angles of incidence and refraction, respectively. Light can always pass from a lower refractive index medium to a higher refractive index medium, because in that case angle I' is smaller than angle I. However, when a beam of light passes from an optically denser medium (having a higher index of refraction n) to an optically rarer medium (having a lower index of refraction n'), the angle of refraction I' is always greater than the angle of incidence I. As the angle of incidence I increases, the angle of refraction I' increases at a faster rate. When $\sin I = n'/n$, then $\sin I' = 1.0$ and the angle of refraction I'=90 degrees. Such an angle of incidence is called the critical angle. When the critical angle condition is met, no light propagates into the optically rarer medium. When the angle of incidence is greater than the critical angle, the light is reflected back into the optically denser medium—a phenomenon called total internal reflection (T.I.R.). If the separating boundary of the two media is smooth and clean, 100 percent of the incident light is reflected back. The critical angle phenomenon is used for measurements of refractive indices of various fluid or solid materials.

FIG. 3a depicts a critical angle refractometer shown and identified broadly by the reference numeral 22. Refractometer 22 is shown as including a housing 32 having an inclined top surface portion 34 and a horizontal top surface portion 36 adjacent thereto, an LCD display 38 and a keypad input 40 at inclined top surface portion 34. A test assembly 24 is situated on horizontal top surface portion 36. Refractometer 22 is similar to the Leica AR600 automatic refractometer available from Leica Microsystems Inc. The Leica AR600 automatic refractometer is manufactured generally in accordance with the disclosure of commonly-owned U.S. Pat. No. 4,640,616 issued Feb. 3, 1987 and entitled AUTOMATIC REFRACTOMETER. The entire disclosure of U.S. Pat. No. 4,640,616 is incorporated herein by reference as if reprinted in its entirety.

The schematic of FIG. 4 illustrates the opto-electronic measurement system of refractometer 22, which is based on the principles of critical angle refractometry described above. The system comprises a photosensitive linear scanned array (LSA) 44 for providing an output signal as a function of the amount and location of light incident thereon. Linear scanned array 44 includes a plurality of closely adjacent and aligned photoelectric cells 46. The measurement system comprises an optical system for directing light onto linear scanned array 44, wherein the amount and location of light illuminating the LSA depends on the index of refraction of a test sample 51. As shown in FIG. 4, the optical system includes a light source 48 and a prism 50 for receiving light along an optical path 57 from source 48. Prism 50 includes a top surface 54 for receiving test sample 51, a bottom surface 56 parallel to top surface 54 through which light enters and exits the prism, and a pair of internally reflective side surfaces 58 and 60, which define acute included angles with bottom surface 56. A temperature sensor 52 is provided at top surface 54 to read sample temperature for temperature compensation purposes.

Light originating from source 48 travels sequentially through a diffuser 62, a polarizer 64, and a collimating lens 66. The parallel light leaving collimating lens 66 enters an interference filter 68 which transmits essentially monochromatic light at a wavelength of 589 nm. A converging lens 70 is arranged to receive light transmitted by filter 68 and concentrate the light in the direction of a reflecting mirror 72, which is orientated to reflect the light through the bottom surface 56 of prism 50. The light is totally internally reflected by side surface 58 to impinge upon top surface 54. A first portion of light (not shown) incident on top surface 54 at the angles less than the critical angle is refracted into sample 51. A second portion of light 55 incident on surface top 54 at the angles larger than the critical angle is totally internally reflected from top surface 54. Second portion of light 55 is then internally reflected by side surface 60 and exits prism 50 through bottom surface 56. After passing through a lens 73, portion 55 is redirected by a reflecting mirror 74 in the direction of linear scanned array 44. Therefore, light distribution at LSA 44 consists of an illuminated region 47, formed by second portion of light 55, and a non-illuminated region 47a. The boundary between the two regions 47 and 47a is referred to as the shadow line, and its position on linear scanned array 44 is dependent upon the refractive index of test sample 51.

In the Leica AR600 automatic refractometer, the LAS contains almost 2600 individual charge-coupled device (CCD) elements, each of which is a 11 $\mu m^2$ square. Each CCD, pixel, is capable of converting the intensity of light hitting upon it into an electrical voltage, which is subsequently converted to a digital number between 0 and 255 by supporting circuitry. Each CCD produces a numeric intensity value as an output reading. A typical graph, illustrating illumination intensity from a bare prism (a reference reading of air) as a function of a cell number, is shown in FIG. 5a. The reference reading of air in FIG. 5a is taken by pressing an INITIATE key of keypad input 40 to provide a reference curve 100, corresponding to the illumination distribution at linear scanned array 44 without a sample on top surface 54 of prism 50. When a sample is placed on the prism, the first portion of the light is transmitted through the sample, and second portion of light 55 is reflected toward the LSA, illuminating a part of it, thus, forming a shadow line on the LSA, as described above with regard to FIG. 4. Determination of the shadow line location expressed as the crossover cell number is carried out by a software routine stored in the programmable memory of refractometer 22. During a reading, reference curve 100 is scaled by 94%, as indicated by the dashed curve just below reference curve 100 in FIG. 5b, forming a scaled reference curve 120. The scaling parameter does not have to be 94%, it can vary (80%, 85% for example) to achieve the best precision between consecutive readings. The crossover cell number is then found by a routine, which identifies the cell or cell fraction at which a sample curve 110 intersects with scaled reference curve 120. The crossover cell number is then converted to a refractive index value, based on a calibration reading of a substance of a known refractive index.

Despite the fact that the critical angle reflection phenomenon has been known in the past, there has been no successful effort to bring critical angle refractometers into the analytical art as sensors, capable of detecting and monitoring binding between an analyte and a binding layer having specific affinity to the analyte. Since critical angle refractometers, such as, for example, the above-described Leica AR600 automatic refractometer are inexpensive, compared to commercially available SPR sensors, it would be desirable to use a critical angle refractometer to sense and monitor binding phenomena. Therefore, the need exists to provide a method and device utilizing critical angle refractometry to sense and monitor the presence and the amount of a particular analyte by measuring changes in the refractive index occurring due to specific binding of the analyte to an immobilized binding layer on a sensing surface.

SUMMARY OF THE INVENTION

Therefore, it is an object of the present invention to provide a sensing device and method utilizing critical angle refractometry to sense and monitor binding interactions between a sample analyte and a binding layer.

It is another object of the present invention to provide a sensor device, which does not measure changes in a refractive index by using the surface plasmon resonance phenomenon, and thus avoids the need for experimentally rigorous procedure of immobilization of a binding layer on a thin metallic layer. A related object of the invention is to avoid problems associated with oxidation of a metallic layer and the necessity to provide an intermediate layer between the metallic layer and a glass surface in traditional SPR sensors.

It is a further object of the present invention to provide a critical angle based sensor device, which is affordable to manufacture and simple to operate.

It is yet another object of the present invention to provide a critical angle refractometric method and apparatus for measuring changes in the refractive index at a sensing layer by passing light through an optically transparent arrangement to cause the light to be totally internally reflected at the sensing layer.

It is also another object of the present invention to provide a method and device utilizing critical angle refractometry to sense presence or absence of a sample analyte in a contacting phase by measuring the critical angle of total reflection of light at a sensing layer.

It is yet another object of the present invention to provide a critical angle refractometer and method for measuring the rate of a binding reaction between a binding layer and a sample analyte.

In view of these and other objects, an apparatus and method for sensing presence and the amount of an analyte in a contacting phase are provided by using a critical angle refractometer to sense changes in a refractive index of a sensing layer occurring as the interaction between the sample analyte and an immobilized binding layer progresses over time. The apparatus, according to one of the embodiments of the present invention, comprises an automatic critical angle refractometer for obtaining refractive index data with respect to a sample analyte in operative association with an opto-electronic measurement system of the refractometer, and a computer connected for data communication with the refractometer for processing the data and reporting changes in the refractive index as a function of time.

The refractometer measurement system includes a linear scanned array of photosensitive cells, and an optical system for directing light onto the LSA. The light impinging upon the LSA forms a shadow line, dividing the LSA into an illuminated portion and a dark non-illuminated portion. The location of the shadow line is dependent on the refractive index of a binding layer immobilized on the sensing surface. Depending on whether the sample analyte has bonded with the binding layer, the position of the shadow line will change. Therefore, correlation of the shadow line location to a value, which is a function of the refractive index, such as a concentration of the sample analyte in the contacting phase, can be established. The correlation is carried out by software routines stored in the programmable memory of the refractometer.

In accordance with the present invention, a method of using critical angle refractometry for sensing and monitoring interactions between the analyte and the binding layer is provided. An optical system directs light through one or more optically transparent elements to impinge upon the interface between the binding layer and one of the optically transparent elements. The absence or presence of binding between the analyte and the binding layer changes the refractive index of the binding layer. The refractive index of the binding layer, in turn, affects the critical angle of total reflection. The light reflected from the interface at a particular angle impinges on the LSA, creating a shadow line, the location of which can be related to the amount of the analyte bonded to the immobilized binding layer. The same principle enables the method and apparatus of the present invention to monitor and measure the rate of changes in the refractive index, which rate is proportional to the concentration of the analyte in a contacting phase and the strength of affinity between the analyte and the binding layer.

The present invention also provides an apparatus and method for sensing the presence or absence of a particular analyte having specific affinity to the binding layer by measuring changes of the refractive index at the binding layer. Such sensing can be implemented in laboratory tests and home test kits. The method comprises directing a collimated light beam at a particular incident angle through one or more optically transparent elements to impinge upon the interface between the binding layer and one of the optically transparent elements. Depending on whether a particular analyte with specific affinity to the binding layer is present or absent in the contacting phase, the incident angle of light will or will not satisfy the condition for total internal reflection. If the condition for total internal reflection is satisfied, the reflected light will impinge on the LSA or any other sensor capable of detecting light, disposed along the optical path of the reflected light. Therefore, depending on whether the sensor is illuminated by totally internally reflected light, the presence or absence of the analyte can be determined. It is also contemplated that the LSA can be disposed to sense transmitted light, which will illuminate the LSA depending on whether the T.I.R. condition is satisfied. An apparatus for practicing the above-described method comprises a collimated beam of light directed at the interface at a particular angle of incidence. In order to sense the critical angle of total reflection, a single light source capable of moving and changing the angle of incidence is provided. In an alternative embodiment of the apparatus, a plurality of light sources directing light beams at the interface at different angles, are utilized to sense the presence or absence of the analyte. Depending on whether the binding between the analyte and the immobilized binding layer has occurred, the light from one of the light sources becomes totally internally reflected at the interface, therefore, illuminating the light sensor and indicating the presence or absence of the analyte.

In one of the embodiments of the invention, a specialized test assembly allows for operative association between the sample analyte in a contacting phase and the immobilized binding layer. In the preferred embodiment, the apparatus includes a thin, optically transparent element having a selected type of ligands immobilized on an upper surface thereof, forming a binding layer. A flow cell is arranged closely above the transparent element for providing a buffer flow of the contacting phase containing the sample analyte intended for specific binding interaction with the immobilized binding layer. An O-ring or a gasket arranged on the upper surface of the disc is sized to provide a peripheral fluid-tight seal between the binding layer on the sensing surface of the element and the flow cell. A high refractive index coupling liquid is provided between a lower surface of the optically transparent element and the top surface of the refractometer prism. The transparent elements, such as discs, are preferably formed of glass, polystyrene, polycarbonate, or other optically transparent materials with a suitable index of refraction. A particular immobilization technique usually depends in part on the material used to form the disc. By way of example, an antibody, such as an anti-strepavidin antibody, may be immobilized on the upper surface of the optically transparent disc, and its antigen strepavidin introduced in a buffer flow for analysis of binding interactions. By way of further example, with respect to DNA binding protein/DNA ligand interactions, the OccR protein may be immobilized on the upper surface of the optically transparent disc, and its oligonucleotide target introduced in a contacting phase for analysis of binding interactions.

To summarize, the present invention provides a method of using critical angle refractometry for sensing presence or absence of an analyte at a binding layer, the method comprising providing a first optically transparent element and a second optically transparent element, the first optically transparent element having a higher refractive index than that of the second optically transparent element, the second element having the binding layer, providing a contacting phase, allowing the contacting phase to contact the binding layer of the second optically transparent element, passing light through the first and the second optically transparent elements to cause the light to impinge upon an interface between the second optically transparent element and the binding layer, and detecting a location of a boundary between a light area and a dark area on a sensing element, the location of the boundary being indicative of the presence or absence of the ligands at the binding layer. The method further provides a contact layer coupling the first optically transparent element to the second optically transparent element. The contacting phase can be liquid, the second optically transparent element is selected from the group consisting of glass and plastic. The binding layer is selected from the group consisting of carboxymethylated dextran, aldehyde activated dextran, hydrazide activated dextran, silanated surfaces, silanized surfaces, silane, aviden, streptaviden, neutraviden, biotinyl, bifunctional spacer arms, self assembled monolayers, lipids and unchanged or uncoated surface of the second optically transparent element. The contacting phase containing the analyte comprises selecting the analyte from the group consisting of antigens, proteins, glycoproteins, vitamins, microbes, pieces of microbes including bacteria and bacterial fragments, viruses, pieces of viral material, lipids, carbohydrates, toxins, DNA, RNA, DNA and RNA analogs, pathogenic organic molecules, anti-bacterial and anti-viral organic molecules and their analogs, therapeutic agents and drugs.

Another embodiment of the invention is a method of using critical angle refractometry for sensing presence or absence of an analyte at a binding layer of a first optically transparent material, the method comprising providing the first optically transparent material of a higher optical density than that of the binding layer contacting the binding layer with a contacting phase passing light along an optical path through the first optically transparent material to cause the light to impinge upon an interface between the binding layer and the first optically transparent material sensing a boundary between a light area and a dark area on a sensing element disposed along the optical path, and utilizing the location of the boundary to determine the presence or absence of the analyte at the binding layer. The optically transparent material is selected from the group consisting of glass and plastic.

Yet another embodiment of the invention is a method for sensing presence or absence of an analyte at a binding layer, the method comprising providing an interface between the binding layer and an optically transparent element, the interface being located along an optical path, the binding layer and the optically transparent element having different optical densities sufficient to totally internally reflect light impinging on the interface, contacting the binding layer with a contacting phase, illuminating the interface with the light propagating along the optical path, so that a portion of the light totally internally reflected from the interface propagates between the interface and a sensing element disposed along the optical path and illuminates the sensing element to form a light area thereon, and detecting a location of a boundary between the light area and a dark area on the sensing element, the location of the boundary being indicative of the presence or absence of the analyte at the binding layer. The portion of the light propagating between the interface and the sensing element comprises light reflected from the interface or transmitted through the interface.

Another embodiment of the invention is a method of sensing presence or absence of an analyte at a binding layer comprising providing a light beam generated by a light source, providing an interface between the binding layer and an optically transparent element, the binding layer and the optically transparent element having optical densities sufficient to cause the light beam impinging upon the interface to be totally internally reflected, contacting the binding layer with a contacting phase, illuminating the interface by the light beam impinging upon the interface at a predetermined angle of incidence, providing a sensor located at a position in which the sensor can sense the light totally internally reflected at the interface, and sensing the presence or absence of light by the sensor, the presence or absence of light being indicative of the presence or absence of the analyte at the binding layer. The method further comprises altering the predetermined angle of incidence by moving or rotating the light source or by moving or rotating the optically transparent element. The method also comprises providing a plurality of light sources so that altering the angle of incidence is accomplished by illuminating the interface by a light beam from a different light source. The described sensor can comprise a plurality of sensing elements.

And yet another embodiment of the invention is a system for detecting presence or absence of an analyte in a contacting phase, the system comprising an optically transparent element having a binding layer deposited thereon, the binding layer having affinity to the analyte a critical angle refractometer defining an optical path of a collimated light beam impinging upon an interface between the binding layer and the optically transparent element, the contacting phase contacting the binding layer, and a sensor disposed along the optical path to detect changes in an optical density of the binding layer by sensing light travelling along the optical path. The system further comprises a test assembly serving to bring the contacting phase in contact with the binding layer, wherein the optically transparent element is a disposable slide and wherein the contacting phase is a biological fluid. The system further comprises a plurality of light sources, wherein each light source is capable of directing a light beam toward the interface at a predetermined angle of incidence and wherein the sensor comprises a plurality of sensing elements.

The present invention also encompasses a method of monitoring specific binding during a particular reaction involving an analyte, the method comprising immobilizing a binding layer on an optically transparent element; bringing the transparent element into operative association with an opto-electronic measurement system of an automatic critical angle refractometer, introducing a contacting phase containing the analyte to contact the binding layer, using the critical angle refractometer to generate measurement data, including data that are a function of the refractive index of the binding layer, at regular intervals over time, and processing the measurement data to permit analysis of the progress of specific binding of the analyte to the binding layer.

BRIEF DESCRIPTION OF THE DRAWINGS

The nature and mode of operation of the present invention will now be more fully described in the following detailed description of various embodiments taken with the accompanying drawing figures, in which:

FIG. 4 is a schematic representation of an opto-electronic measurement system of the automatic refractometer shown in FIG. 3a;

FIG. 10b is a number of graphs containing fitted data corresponding to FIG. 10a;

FIG. 11b is a number of graphs containing fitted data corresponding to FIG. 11a;

FIG. 13b is a number of graphs containing fitted data corresponding to FIG. 13a;

FIG. 16b is a graph illustrating changes of light intensity in the trial corresponding for FIG. 16a;

FIG. 16c is a graph illustrating changes in the position of the shadow line in the trial corresponding to FIG. 16a;

FIG. 16d is a graph illustrating the position of the shadow line at the beginning of the trial corresponding to FIG. 16a;

FIG. 17b is a perspective bottom view of the slide depicted in FIG. 17a;

DETAILED DESCRIPTION OF THE INVENTION

In the following detailed description of the invention, reference is made to the accompanying drawings, which form a part hereof, and in which specific preferred embodiments for practicing the invention are shown by way of illustration. These embodiments are described in sufficient detail to enable those skilled in the art to practice the invention, and it is to be understood that other embodiments may be utilized and that logical, mechanical, chemical and electrical changes may be made without departing from the spirit and scope of the present invention. The following detailed description is, therefore, not to be taken in a limiting sense, and the scope of the present invention is defined only by the appended claims.

To carry out the objects and principles of the present invention, an automatic critical angle refractometer was used to sense the shadow line on a photo sensor, such as an LSA, and, therefore, resolve the critical angle of total reflection of a contacting phase, placed on an optically transparent element with a binding layer on it. The binding layer comprised the ligands with specific affinity to the analyte in the contacting phase. (Throughout this description the words "sample" and "contacting phase" are used interchangeably). When the analyte bonded to the binding layer, the optical density of the binding layer changed. In several experimental trials, described in detail below, a critical angle refractometer was used to detect changes in the optical density of the binding layer occurring as a result of the binding phenomena. The experimental results described below demonstrated that small refractive index changes, occurring as a result of binding between the binding layer and the sample analyte, could be detected using the optoelectronic configuration of the present Leica AR600 automatic refractometer, which provides refractive index measurement over a relatively broad range of indices. The results of the experimental trials proved that critical angle refractometry can be successfully used to detect and monitor changes in the optical density at the binding layer, which changes are caused by binding interactions between the analyte and the binding layer.

Figure 7:
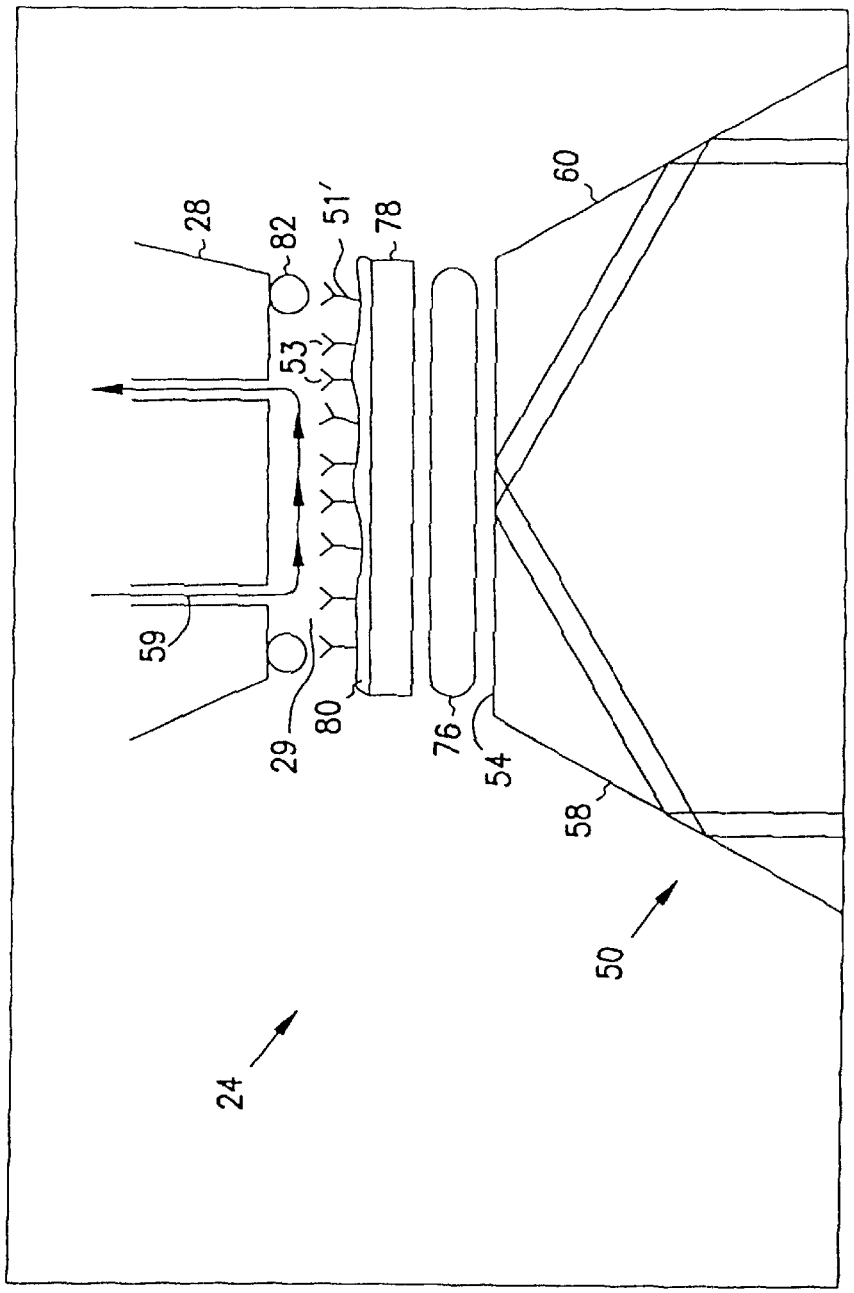
FIG. 7 is a schematic exploded view of the preferred test assembly of the present invention.

FIG. 7 shows a test assembly 24 for performing refractometric measurements in the preferred embodiment of the present invention. FIG. 7 shows the test assembly in slightly exploded detail. Test assembly 24 includes a high index coupling liquid 76, introduced directly to top surface 54 of prism 50 of critical angle refractometer 22 (not shown), an optically transparent element, such as disc 78, with a binding layer 51', deposited on an interface 80 between disc 78 and the binding layer, and a sealing O-ring 82 interposed between flow cell 28 and interface 80. In this embodiment prism 50 is a sapphire prism with the refractive index of about 1.7.

Binding layer 51' comprises ligands 53 immobilized on interface 80. Ligands 53 may or may not have specific binding affinity to the sample analyte contained in a contacting phase 59. In the preferred embodiment of the present invention, contacting phase 59 is a liquid phase, delivered through flow cell 28 to contact binding layer 51'. After the contact, the sample analyte in phase 59 contacts ligands 53 and binds to the ligands, provided that the analyte and the ligands have specific affinity to each other, allowing the binding phenomena to occur. An example of binding layer 51' is an antibody matrix immobilized on interface 80. Contacting phase 59, such as, for example, an antigen solution for interaction with the antibody matrix of layer 51', is delivered by flow cell 28, and the binding interaction is then monitored by means of critical angle refractometry.

Flow cell 28 can be a conventional flow cell. In one of the embodiments of the present invention, a flow cell capable of providing a flow rate of about 1 ml/minute, such as that available from Leica Microsystems Inc. under Catalog No. 10610, covers a substantial portion of interface 80. A suitable coupling liquid 76 is high refractive index oil, preferably 1.63 refractive index oil. Transparent disc 78 can be formed of a material that is optically transparent to the incident light, such as, for example, glass, plastic, or other optically transparent materials with a suitable index of refraction. In the described embodiment, the wavelength of incident light is 589 nm. In the preferred embodiment, disc 78 has a refractive index greater than 1.52 at 20'C. Such materials are, for example, glass, polystyrene, or polycarbonate. A suitable thickness for discs 78 used in experimental trials was 0.17 nm.

Figure 7A:
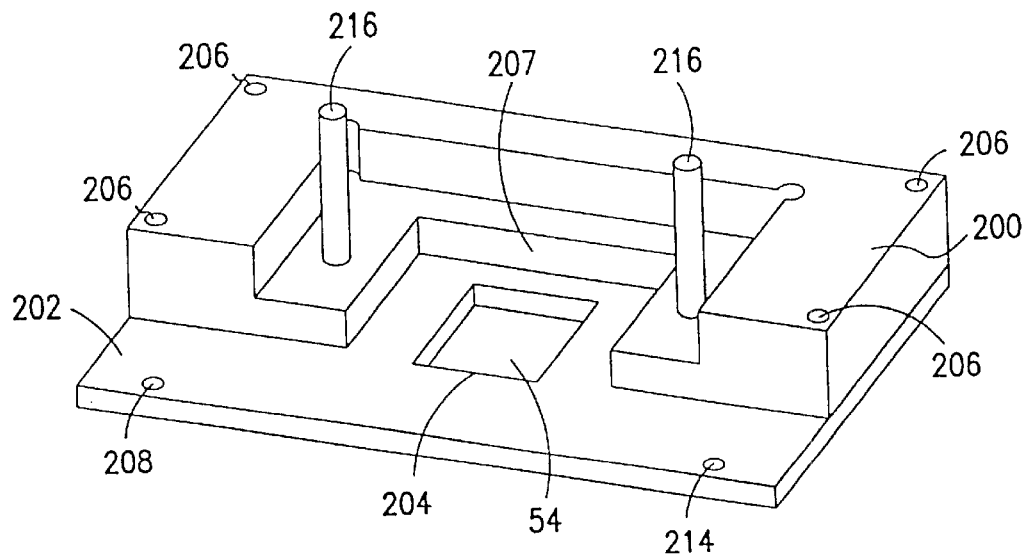
FIG. 7a is a perspective view of a base and a plate of an embodiment of the present invention.
Figure 7B:
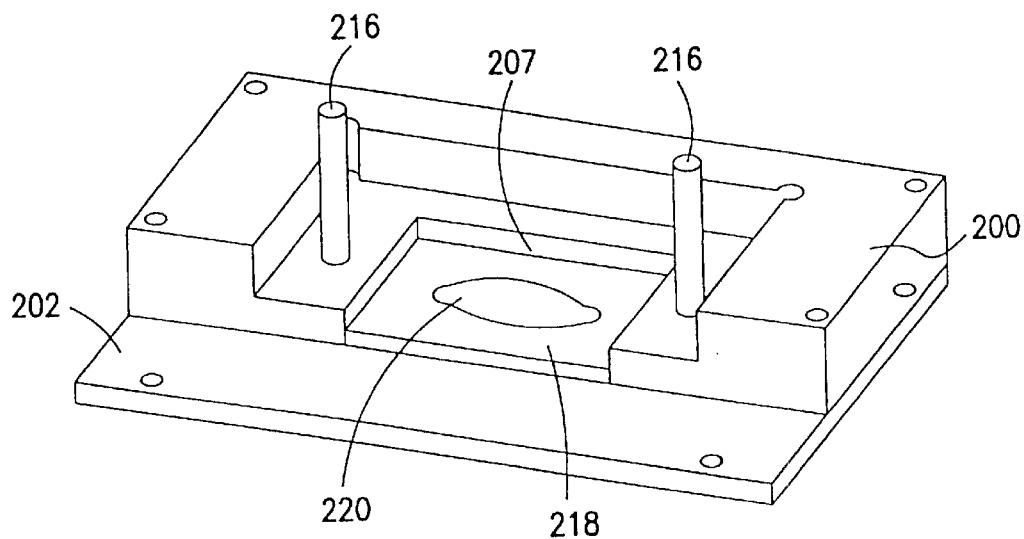
FIG. 7b is a perspective view of a base and a plate with a slide.
Figure 7C:
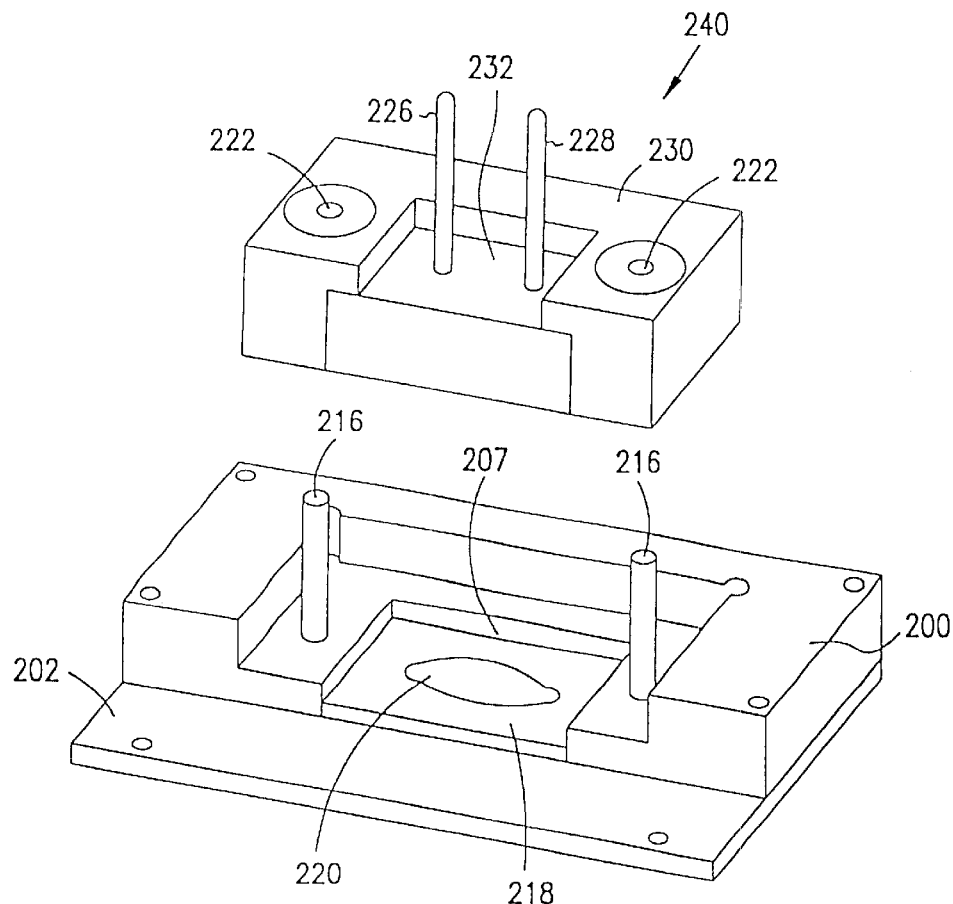
FIG. 7c is a perspective view of a flow cell cap.
Figure 7D:
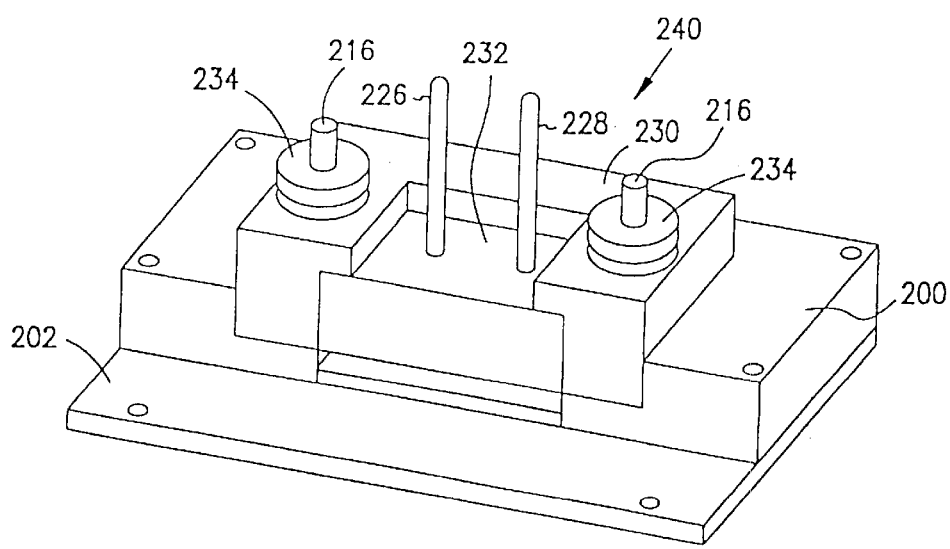
FIG. 7d is a perspective view of an assembled flow cell/slide embodiment.
Figure 7E:
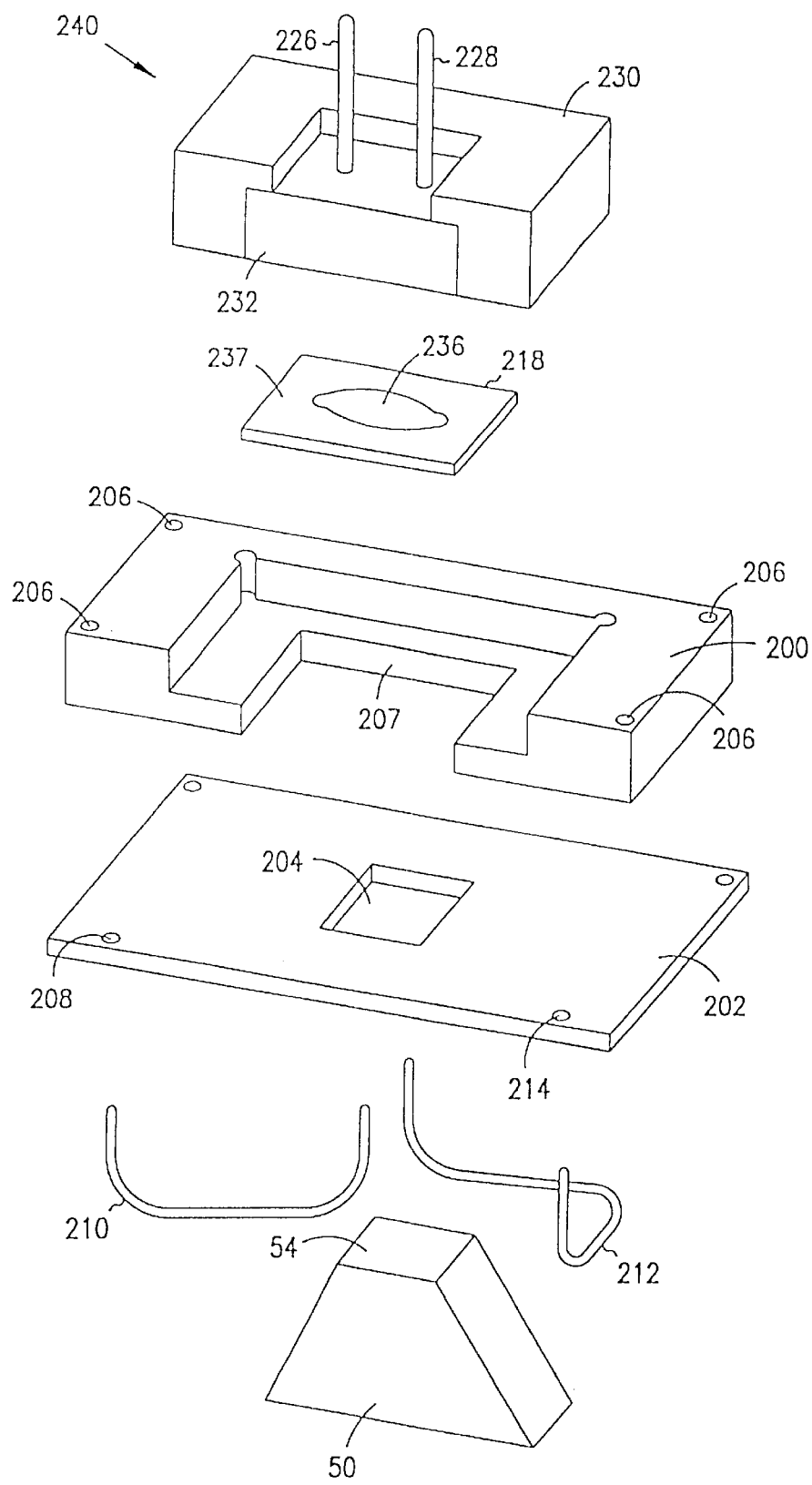
FIG. 7e is an exploded view of the embodiment illustrated in FIGS. 7a–7d.

Another embodiment of a flow cell/transparent disc test assembly is illustrated in FIGS. 7a–7e. In that embodiment a base 200 of the flow cell is placed on a plate 202, which plate has an opening 204 exposing top surface 54 of prism 50 (prism not shown), as shown in FIG. 7a. Base 200 can be attached to plate 202 by any convenient means, including simply placing the base on the plate, or using screws or other equivalent means to fasten the base to the plate through openings 206, as shown in FIG. 7a. A drop of coupling liquid 76 (shown in FIG. 7) is put on top surface 54 either manually or by bringing liquid 76 to top surface 54 by dropping the liquid into a first plate opening 208. The liquid then travels through a first tube 210 connected to a ate opening 208 and reaches surface 54. If an excess amount of coupling liquid 76 is brought to top surface 54, a second tube 212 drains the excess liquid from top surface 54 to a second plate opening 214, as illustrated in FIG. 7e.

FIG. 7b shows base 200 and plate 202 with an optically transparent slide 218 (similar to transparent disc 78 described above) placed on plate 202. Slide 218 is disposed above top surface 54 of the prism and inside a frame 207 in base 200 suitable for receiving the slide. Frame 207 defines the location of slide 218 relative to top surface 54 of the prism. In FIG. 7b frame 207 is rectangularly shaped to receive a rectangular slide 218 and to partially surround the slide. As can be seen in FIG. 7e, in one of the embodiments slide 218 comprises an optically transparent area 236 with a binding layer attached to it, and a frosted area 237 for trapping and diffusing light illuminating area 237. Area 237 can be etched and mechanically reduced with an abrasive to produce the frosted finish.

FIG. 7c illustrates a cap 240 of the flow cell with tubes 226 and 228 for circulating a contacting phase through the flow cell. Cap 240 comprises a cap frame 230 with holes 222. One or more threaded studs 216 protruding from base 200 pass through the holes 222 in cap frame 230 which is then secured in place preferably by knurled nuts 234, as illustrated in FIG. 7d. Tubes 226 and 228 are coupled to the flow cell via a top portion 232 fitting into cap frame 230, as shown in FIGS. 7c, 7d, and 7e. Top portion 232 can be attached to cap frame 230 either permanently or removably. Tubes 226 and 228 deliver contacting phase 59 (shown in FIG. 7) to slide 218. The contacting phase enters the flow cell through one of the tubes 226 or 228, flows over the slide and exits the flow cell through the other tube. It is contemplated that top portion 232 can comprise a temperature sensor or any other sensor measuring various properties of the fluids circulating in the flow cell. Such a sensor would be disposed on the surface of top portion 232 normally in contact with the contacting phase during the operation of the refractometer.

Figure 17A:
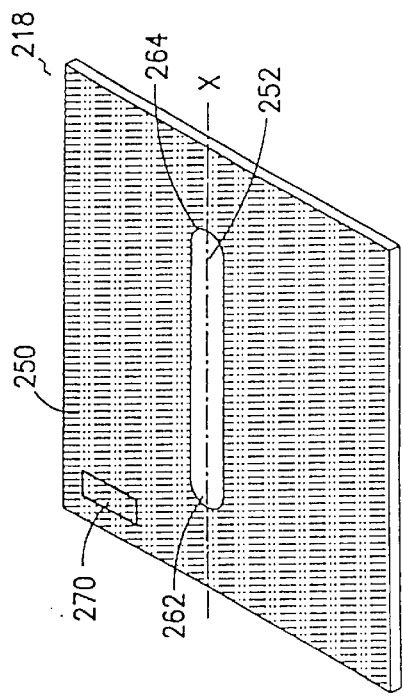
FIG. 17a is a perspective top view of a slide of the present invention.
Figure 17B:
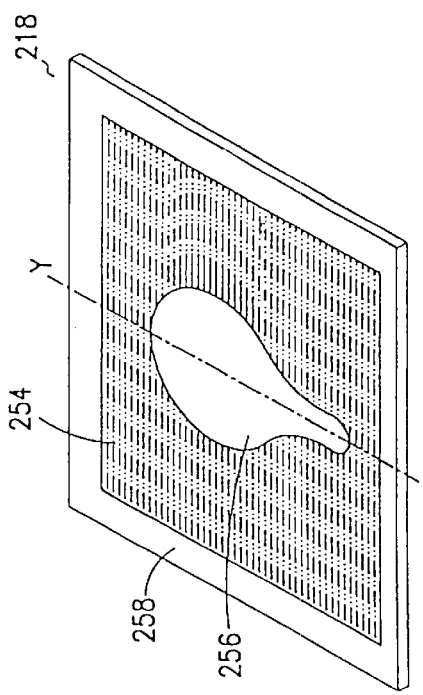
Figure 17C:
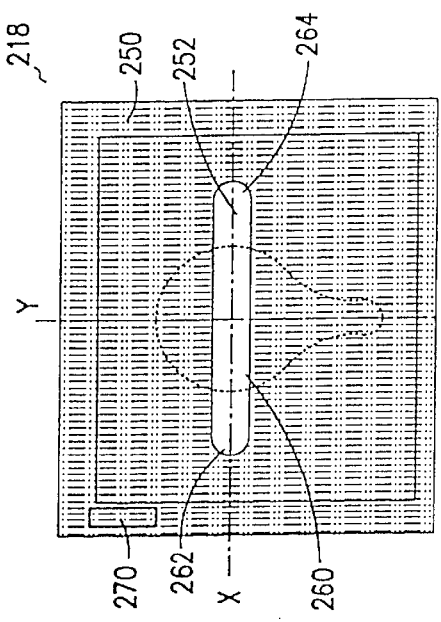
FIG. 17c is a bottom view of the slide.
Figure 17D:
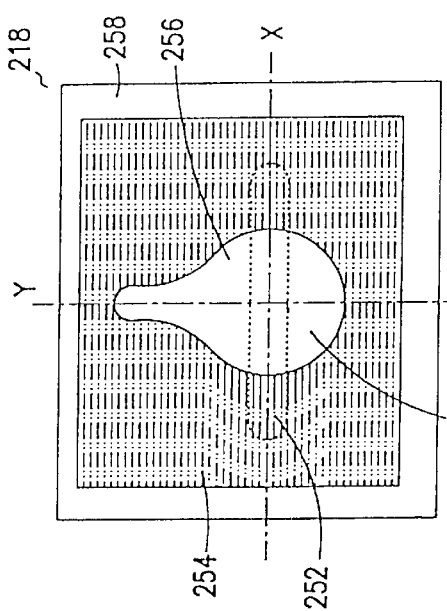
FIG. 17d is a top view of the slide.
Figure 17E:
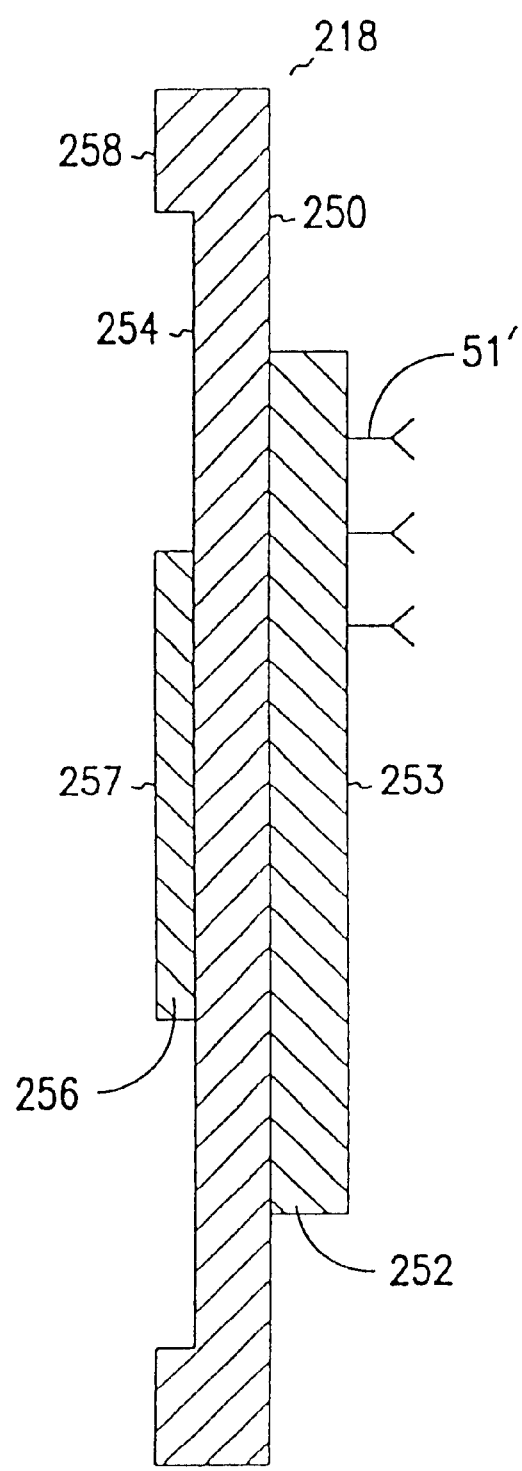
FIG. 17e is a cross sectional side view of the slide depicted in FIGS. 17a–17e.

A particular geometry and design of slide 218 used in the flow cell assembly described with regard to FIGS. 7a–7e are shown in more detail in FIGS. 17a–17e. Slide 218 is shown to have an upper surface 250 with a first raised portion 252 (FIG. 17a). Upper surface 250 has a frosted finish, diffusing or trapping unwanted light and preventing it from entering the sensing system and being detected by the light sensor. Frosted finish can be achieved by chemical or mechanical etching or any other means contemplated by a particular application. First raised portion 252 is not etched and remains optically transparent to light. A cross-sectional side view of slide 218 shown in FIG. 17e illustrates a raised portion 252 having a sensing surface 253 onto which binding layer 51' is attached. In one of the embodiments illustrated in FIGS. 17a–17d first raised portion 252 is shaped as an oval having a longitudinal axis X. A gasket 220, shown in FIG. 7b, is usually placed over first raised portion 252 to seal the area of circulation of the contacting phase during the measurement time. Gasket 220 In FIG. 7b is oval shaped to parallel the shape of first raised area 252 in FIG. 17a.

A lower surface 254 of slide 218 in FIG. 17b is similar to upper surface 250, the frosted finish of lower surface 253 prevents unwanted light from entering the sensing system of the refractometer. A second raised portion 256 is not etched and remains optically transparent to light. Second raised portion in one of the embodiments is tear-drop shaped with a longitudinal axis Y perpendicular to axis X. A third raised portion is also transparent to light and comprises a rim 258 which contacts plate 202 (shown in FIG. 7a) when the slide is placed on the plate. Coupling liquid 76 delivered to top surface 54 of the prism contacts second raised portion 256 and couples slide 218 to top surface 54, as illustrated in FIG. 7b.

As follows from FIGS. 17c–17d, an area of transparent overlap 260 defined by raised portions 252 and 256 is the area where the light traveling through slide 218 and illuminating surface 253 will be reflected or transmitted, indicating the presence or absence of the binding reaction between binding layer 51' and the analyte in the contacting phase. As shown in FIG. 17d, the oval-shaped portion 252 extends beyond the overlap area 260 from a first end 262 to a second end 264. A contacting phase in the flow cell usually first contacts slide 218 either at first end 262 or second end 264. By the time the contacting phase travels from either first end 262 or second end 264 and to overlap area 260, any turbulence in the contacting phase is reduced and the flow of the contacting phase becomes laminary, improving the precision of the measurements of the binding reaction on the sending surface.

As illustrated in FIGS. 17a and 17d, the present invention contemplates that surface 250 of slide 218 comprises a code area 270, which contains an indicium or an embedded chip. The indicium contained in code area 270 can be a readable optical pattern providing information about a particular binding layer attached to the slide, refractive index of the material of the slide, or a particular slide in any desired way. The indicium also can be used to ascertain that the slide is correctly inserted into the flow cell before the beginning of the measurement session. If code area 270 contains a chip, the chip can be responsive to certain energy (such as, for example, radio frequency energy) with a distinctive coded signal. In response to distinctive coded signal the chip will provide information about a particular slide, the binding layer attached to the sensing surface, the orientation of the slide and any other desired information. Code area 270 can be located on any surface of the slide or inside the slide, depending on a particular design of the slide, the flow cell and the refractometer.

It should be noted that other geometries and designs of slide 218 with a binding layer on it can be used without departing from the scopes of the claims of the present invention.

It is noted that the use of transparent disc 78 for supporting the binding layer is preferred, but not necessary in all instances for practicing the present invention. This is so, because, for example, binding layer 51' can be immobilized directly on prism 50 without disc 78. In that case the sample analyte in contacting phase 59 contacts ligands 53 immobilized directly on prism 50. In such an arrangement, as well as other possible arrangements, as long as the condition of total internal reflection is satisfied, refractometric measurements of binding phenomena can be performed.

Indeed, various arrangements can be used for fulfilling the condition of total internal reflection at interface 80 in order to resolve the critical angle. For example, a photo sensor can be positioned to sense either the portion of light, which was totally internally reflected at the interface (as in the preferred embodiment of the invention), or the portion of light transmitted through the interface into the binding layer. In both cases the position of the shadow line on the sensor will be indicative of the refractive index of the binding layer and, therefore, of the binding phenomena taking place at the binding layer. Additionally, interface 80 can be illuminated with either transmitted or reflected light. The condition for total internal reflection can be also met, when the interface is illuminated through any optical system, not necessarily the optical system, which includes a prism directing light onto the interface. Such optical systems as, for example, lens or mirror arrangements directing the light onto the interface can be successfully used in the present invention. As long as the light incident on interface 80 illuminates the interface at the angles, satisfying the total internal reflection condition, the refractometric measurements of the binding phenomena can be made.

By way of example, but not limitation, various binding layers, suitable for use with the critical angle refractometer of the present invention, can comprise the following ligands, immobilized on transparent disc 78. The first example is a carboxylated dextran coated glass disc. In that example, a layer of dextran is first chemically bound to the surface of transparent disc 78 made of glass. After the dextran has been immobilized on disc 78, it can be modified with one of the several different chemicals containing a carboxyl group as a terminal end of the dextran molecules. The modification step provides carboxymethyl groups, which can be used to bind such ligands as proteins by well-known EDC/NHS chemistry. Examples of the chemicals used at the modification step include chloroacetic, bromoacetic, and 6-bromohexanoic acids. After the dextran has been modified, direct immobilization of such binding layers as proteins to the carboxyl group can be accomplished, further modification of the dextran can be performed to attach to it a terminal amine group using the known EDC (1-ethyl-3-(3-dimethylaminopropyl)carbodiamide) chemistries.

Another example of a binding layer includes silane molecules covalently bound to the —Si—OH groups on the surface of disc 78 made of silica. Depending upon the functional groups located at the terminal end of the bound silane molecules, direct immobilization of proteins can be accomplished. Alternatively, further surface modifications, i.e. attachment of molecules to the silane molecules, can make other functional groups available for protein (ligand) immobilization. Examples of commercially available silane molecules are γ-glycidoxypropyl triethoxysilane and 3-aminopropyl triethoxysilane. The functional groups at the terminal ends of these silane molecules (the ends where immobilization of a binding layer occurs) are hydroxyl and amine groups, respectively. Alternatively, bifunctional groups, such as gluteraldehyde, may be attached to the silane, and then the ligands are attached to the group. The bifunctional groups are used as spacer arms in order to minimize steric effects and provide access to active sites of the ligands To obtain an aviden/streptaviden coated glass disc, aviden or streptaviden is bound to the glass surface of disc 78, using chemistries similar to those described in the silanization procedure. Once silane is bound to the glass surface, then aviden/streptaviden is attached to a bifunctional spacer arm. Since the bioten-aviden interaction is characterized by one of the highest available affinities, the surface with attached aviden/streptaviden possesses an extremely high affinity for biotin. Biotinylated proteins can then be easily bound to the coated glass by merely bringing biotinylated proteins into contact with aviden.

In another example of binding chemistry, biotin molecules are bound to the surface of disc 78 made of glass, creating the initial biotinylated glass surface. The binding is accomplished by using chemistries similar to those described in the silanization procedure, resulting biotinylated glass. The aviden/streptaviden molecules are then selectively adsorbed on the biotinylated glass surface, thus creating a surface with high affinity for biotin molecules, similar to the surface of the aviden coated glass. Biotinylated proteins can then be attached to the surface. In this example, the surface can be regenerated without destroying the initial biotinylated glass surface. Alternatively, aviden/streptaviden/neutraviden conjugated proteins may be directly coupled to the biotinylated glass.

When transparent disc 78 is made of plastic, several binding chemistry techniques are available to immobilize various ligands on the plastic surface. One of the techniques is a passive adsorption of proteins to a hydrophobic plastic material with no modification or activation of the proteins. The preferred hydrophobic material is polystyrene. In that technique electrostatical attraction causes positive charges on a protein "stick" to the negatively charged plastic. By controlling such parameters as pH, ionic strength, and period of incubation, binding of the ligands (proteins) can be accomplished. The period of incubation here is the length of time during which the solution containing the protein is left in contact with the disc surface.

Another available technique involves, as an initial step, binding glutaraldehyde to the plastic surface, leaving the aldehyde group at the terminal end. The aldehyde group is then used to immobilize a protein. Such a technique usually results in increased amount of immobilized protein. Yet another immobilization technique involving plastic surfaces is the technique of using photo-activated cross-linkers. In that technique immobilized enzymes are conjugated with cross-linker molecules and then bound to the plastic surface by exposure to UV light.

It is also contemplated in the present invention that a self assembled lipid monolayer on a clear glass or plastic surface can be used to immobilize membrane bound proteins or other ligands with affinity for the hydrophobic surfaces. Overall, the suitable binding layers can be carboxymethylated dextran, aldehyde activated dextran, hydrazide activated dextran, silanated surfaces, silanized surfaces, silane, aviden, streptaviden, neutraviden, biotinyl, bifunctional spacer arms, self assembled monolayers, lipids and unchanged or uncoated surface of glass or plastic. The suitable analytes can be antigens, proteins, glycoproteins, vitamins, microbes, pieces of microbes including bacteria and bacterial fragments, viruses, pieces of viral material, lipids, carbohydrates, toxins, DNA, RNA, DNA and RNA analogs, pathogenic organic molecules, anti-bacterial and anti-viral organic molecules and their analogs, therapeutic agents and drugs.

Figure 1:
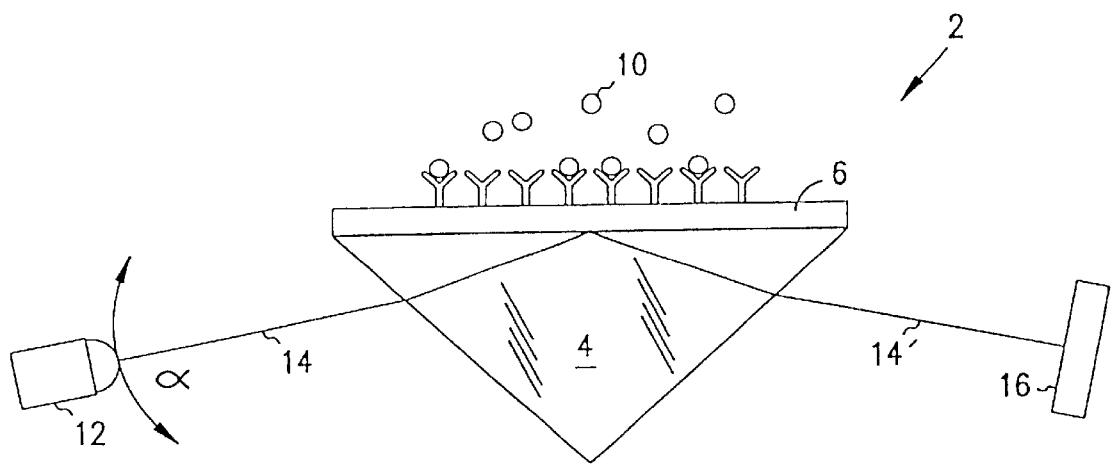
FIG. 1 is a schematic representation of an SPR sensor.
Figure 2:
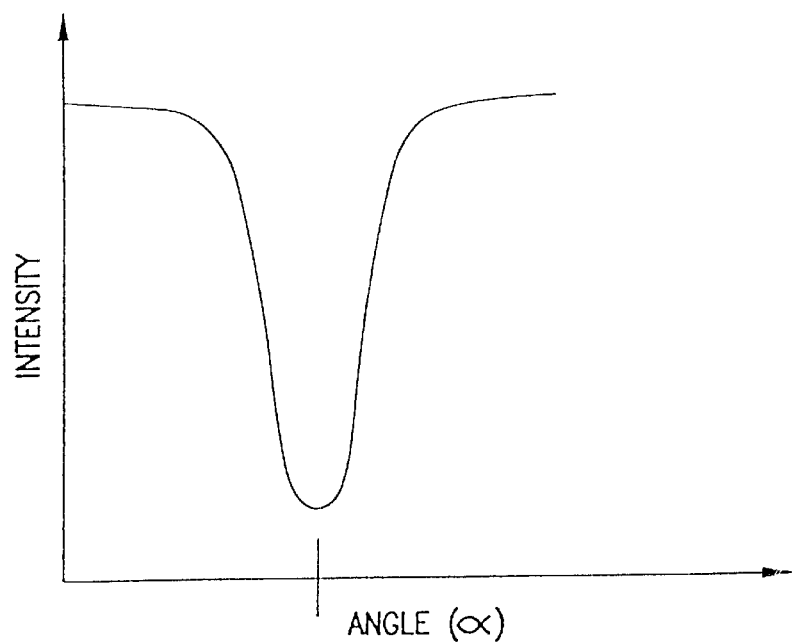
FIG. 2 is a graph of intensity of an SPR sensor as a function of angle of incidence.
Figure 3A:
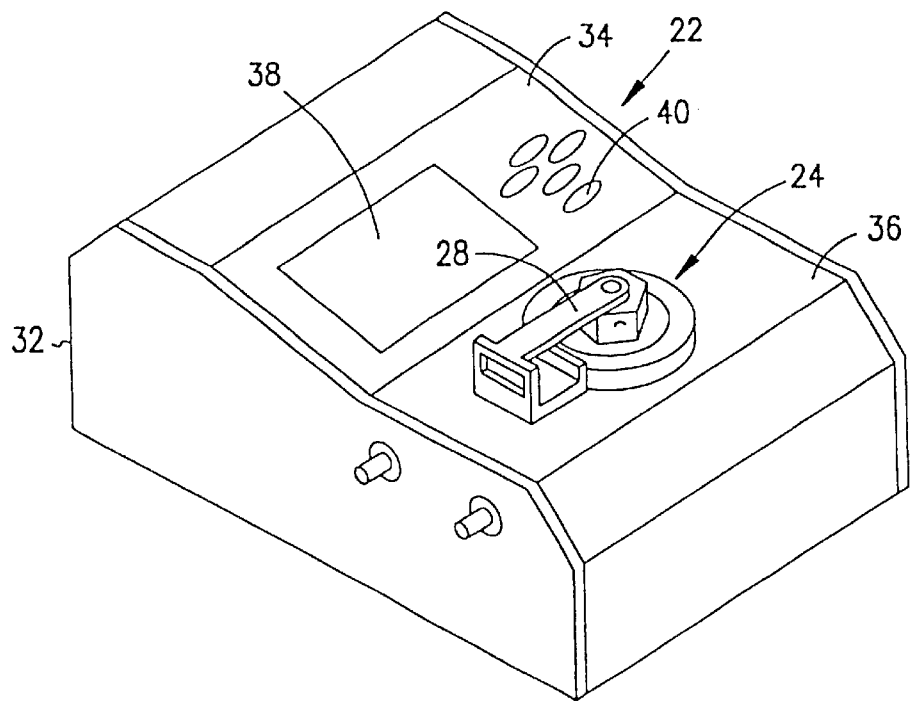
FIG. 3a is a view of a critical angle refractometer.
Figure 3B:
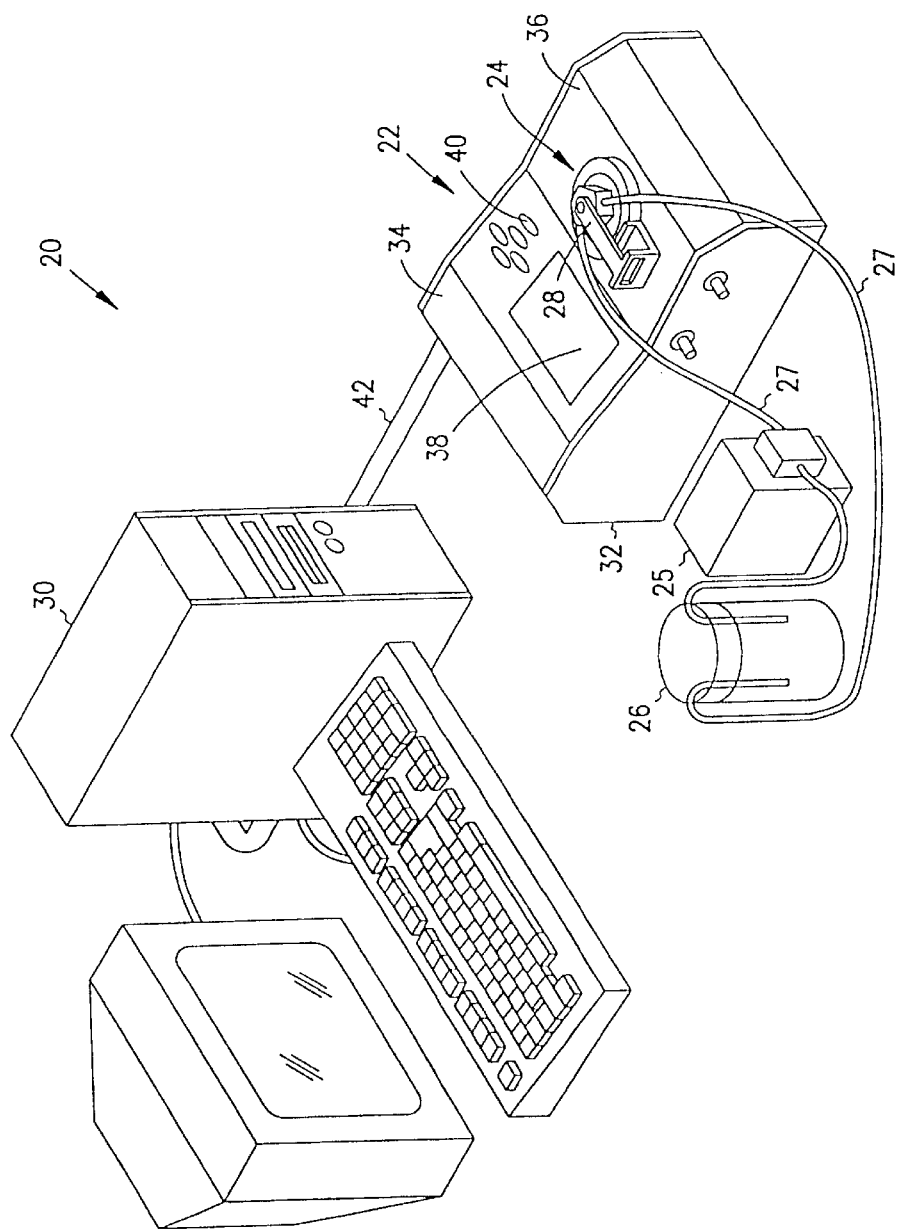
FIG. 3b is a perspective view of a sensor apparatus according to the present invention, including an automatic critical angle refractometer.

In experimental trials described in detail below, refractometer 22 was used in an experimental set up illustrated in FIG. 3b. Shown in FIG. 3b is an experimental set up formed in accordance with the present invention and identified broadly as reference numeral 20. Set up 20 generally comprises automatic refractometer 22 having test assembly 24 thereon for measuring a refractive index , a reservoir 26 for storing a fluid contacting phase, flow cell 28 defining a well 29 (see FIG. 10) adjacent test assembly 24, a pump 25 and flexible tubes 27 for delivering the contacting phase from reservoir 26 to flow cell 28, and a personal computer 30 connected for serial communication with refractometer 22 for controlling measurement functions of the refractometer, and for processing and storing measurement data received from the refractometer.

Refractometer 22 further includes an RS-232 serial port, not shown, for data linking by way of a standard serial cable 42 to a peripheral device, most commonly personal computer 30 having its own serial communications port (COM1 or COM2). Communication between refractometer 22 and computer 30 can be controlled by any terminal communication software program running on the computer. However, the terminal program, which comes with Microsoft Windows 3.11 and the hyperterminal program, which comes with Microsoft Windows 95, are known to enable data communication between refractometer 22 and computer 30 for extracting real time measurement data according to methodology of the present invention. The recommended communications port setup for the terminal program is baud rate—19200, data bits—8, stop bits—1, parity—none, flow control—XON/XOFF. Under the menu option 5 "Settings", then option "Text Transfers", the option "Standard Flow Control" should be chosen. It is helpful to save these settings for future use. As will be understood more fully by reference to the Owner's Manual and supporting documentation for the Leica AR600 automatic refractometer, the refractometer may be controlled remotely from computer 30 through user input and sending of various control codes. While the apparatus of the present invention is generally described herein including automatic refractometer 22 linked to personal computer 30, it is of course possible to provide preprogrammed software and memory within refractometer 22 itself, which enables the instrument to continually perform and record readings at regular chosen intervals for various sensing applications.

It is important to note that in the commercially available Leica AR600 automatic refractometers, a crossover at cell #100 of the LSA corresponds to a refractive index of about 1.3 at 20° C., while a crossover at cell #2450 corresponds to a refractive index of about 1.52 at the same temperature. Since most binding phenomena result in changes of the refractive indices within the range from about 1.3 to about 1.4, the available broad range of refractive index measurements in the configuration of Leica AR600 was successfully used.

By way of overview, seven experiments described herein involved two general stages: first, preparation of a supporting surface and immobilization of a binding layer thereon, and second, continuous measurements of refractive index changes at the interface between the glass and the binding layer by critical angle refractometry. The measurements were taken after additions of a non-binding solution to the contacting phase and during the binding reaction between the sample analyte and the binding layer.

In trials one and two, the mass of the flowing contacting phase was changed by additions of sucrose and Bovine Serum Albumin. The additions were made in order to determine feasibility of measuring refractive index changes at the surface of a glass slide coupled to the prism of the Leica AR600 critical angle refractometer.

In the third and fourth trials, antibody was immobilized by covalent bonding to silanated glass discs, which contained a proprietary spacer arm terminating in an aldehyde group. Measurements were taken for five successively increasing concentrations of antigen added over time in each trial.

In trial five, Neutraviden conjugated Goat Anti-Mouse IgG antibody was adsorbed onto a biotinylated glass surface. In trials six and seven the experiment included the reaction of immobilized Goat Anti-Mouse Antibody with Sheep IgG as a control solution and the specific binding antigen Mouse IgG. The recorded measurement data from experimental trials one through seven are provided in the corresponding drawing figures.

Preparation of transparent discs 78 involved silanyzation and then periodate oxidation of the discs. While silanated glass slides are available commercially and may be useful in practicing the present invention, silanyzation of plano-plano glass plates of a suitable refractive index, which is greater than the expected refractive index of a contacting phase was performed to ensure high quality in trials one and two. The transparent discs 78 used in the experiments were initially cleaned and hydroxylated by consecutive immersion in concentrated sulfuric acid, distilled water, ethanol, and acetone. Five hundred grams of sulfuric acid were acquired from Sigma-Aldrich Chemicals, product number S-1 526, and was of ACS Reagent Grade, 95.7% pure. Transparent discs 78 were immersed once for ten minutes in the sulfuric acid, and then immersed in distilled water three times, for ten minutes each time. The ethanol was acquired from Sigma-Aldrich Chemicals, product number 27,074-1, and was reagent, denatured, HPLC Grade. Transparent discs 78 were immersed in the ethanol twice for ten minutes per each immersion. The acetone was also obtained from Sigma-Aldrich Chemicals and was 99.9% pure, ACS Reagent Grade. The transparent discs were immersed twice for ten-minute periods in the acetone. Various immersions can be carried out by supporting transparent discs 78 on wire support hooks each of which is formed from a single strand of copper wire. Several of these hooks, each having a transparent disc 78 mounted thereon by bending the wire around the disc, were hung from a bar set across the top of a reagent container. As an alternative to individual immersion hooks, one or more racks having an array of regularly spaced open wells for holding transparent discs 78 could be machined specifically for immersion purposes.

Once the transparent discs 78 have been cleaned, they must be activated with 3-aminopropyl, tri-ethoxy silane, hereinafter referred to as APTS. An APTS molecule contains a silicon atom bonded to three ethyl groups via an oxygen atom (tri-ethoxy silane). This portion of the molecule bonds directly to interface 80 of transparent disc 78 during a condensation reaction involving the hydroxy groups on interface 80, and the free protons in the aqueous environment. To perform this reaction for a batch of twenty discs, a 10% wt/vol fresh aqueous solution of APTS is produced by mixing 2.5 ml of APTS with 25 ml of distilled water. This solution was titrated to a pH of 5.0 using Glacial Acetic Acid, obtained from Sigma Aldrich Chemicals, product number A-0808, and an electronic pH meter. The reaction of transparent discs 78 with the coupling agent APTS was controlled at 80° C. for three hours.

Figure 14:
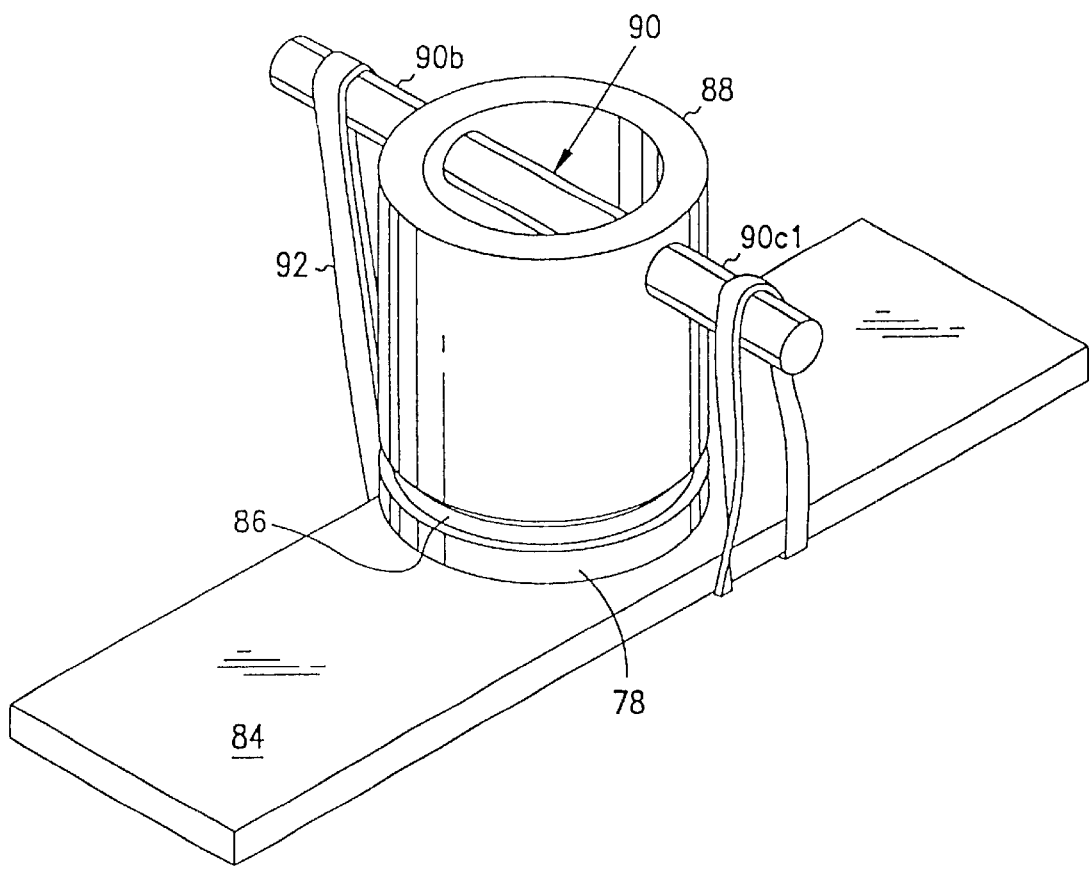
FIG. 14 is a cross-sectional view of an arrangement used for restricting chemical activation to only one side of a transparent disc used to support an immobilized reactant.

FIG. 14 illustrates an arrangement used for restricting chemical activation to only one side of each transparent disc 78. Transparent disc 78 was placed on a narrow, sturdy surface, such as the surface of a transparent slide 84, with the sample surface to be activated facing upwards as shown. A rubber O-ring 86 having an inner diameter of 8–9 mm is placed on top of transparent disc 78. The size of O-ring 86 is chosen to be the same as or slightly larger than the size of O-ring 86 placed between flow cell 28 and transparent disc 78 during the actual refractometric readings to ensure that all of the sample surface exposed to the sample analyte during the refractometric measurements will be activated. A piece of tubing 88 having an inner diameter corresponding to that of O-ring 86 and a height no greater than 25 mm is placed on top of O-ring 86. As will be appreciated, O-ring 86 creates a fluid-tight seal between transparent disc 78 and tube 88. Tube 88 includes a pair of diametrically opposed through-holes at an elevated portion thereof for receiving a sturdy dowel 90 having exposed end portions 90a and 90b. The assembled components are releasably held together by a continuous elastic band 92 looped around one exposed end 90a or 90b of dowel 90, then under slide 84 and around the other exposed end of dowel 90.

After the reaction of the APTS solution with the sample surface 80 of transparent disc 78 is completed, the assembly shown in FIG. 14 was disassembled and transparent discs 78 were heated for two hours at 120 C., then cooled to room temperature. The cooled transparent discs were then soaked in 5% wt/vol glutaraldehyde solution in phosphate buffer. The pH of the phosphate buffer was 6.8. For a batch of twenty to thirty transparent discs, mixing 10 g of glutaraldehyde with 200 ml of phosphate buffer provided a sufficient amount of solution. The transparent discs were soaked for ninety minutes at room temperature (22'C.), followed by two immersions in distilled water for ten minutes each immersion. After the water immersions, the single side activation assembly shown in FIG. 14 was reassembled and a small amount of the antibody was pipetted into the tubing well and allowed to react for twenty-four hours at 40 C. to test coating efficiency. Following the antibody reaction, transparent discs 78 were washed with phosphate buffer and stored in isotonic saline at 4'C. The method of silanyzation is well known, and reference can be made to the publication *Immobilized Affinity Ligand Techniques* by Greg T. Hermanson, A. Krishna Mallia, and Paul K. Smith, Academic Press, 1992, pages 12–14.

To carry out the periodate oxidation step, 600 µl of at least 1 mg/ml antibody solution was extracted and placed in a labeled vial, and 0.06 g of sodium meta-periodate was dissolved in 10 ml of distilled water. Periodate solution was then combined with antibody solution by mixing 300 µl of periodate solution with the antibody solution in the labeled vial, and allowing the combination to react in the dark for thirty minutes to produce aldehyde groups from the carbohydrates. The aforementioned publication *Immobilized Affinity Ligand Techniques* provides protocol for periodate oxidation of a support matrix at page 75 thereof. The next step was to couple the antibody to interface 80 of silanated discs 78. Protocol for this step may be found *Immobilized Affinity Ligand Techniques* starting at page 223.

Figure 5A:
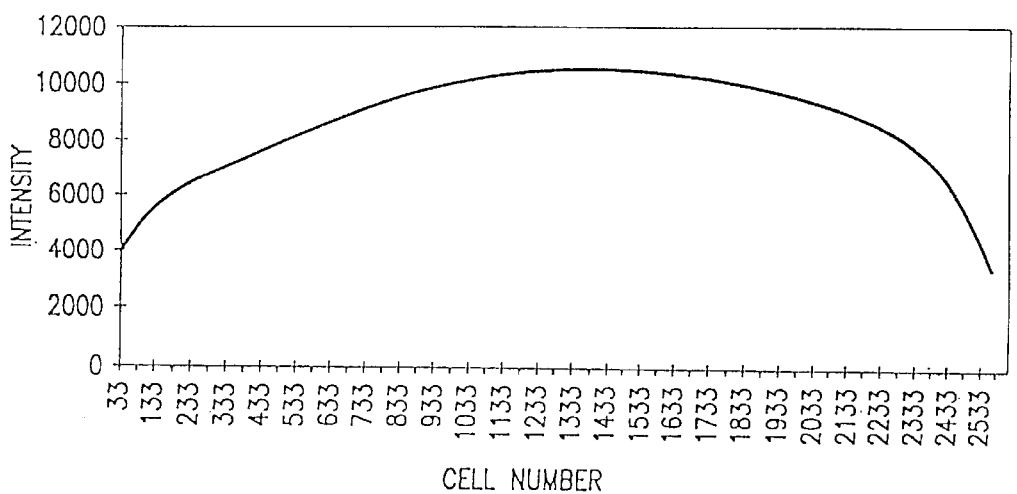
FIG. 5a is a graph illustrating a reference curve of a refractometer initiated in air.
Figure 5B:
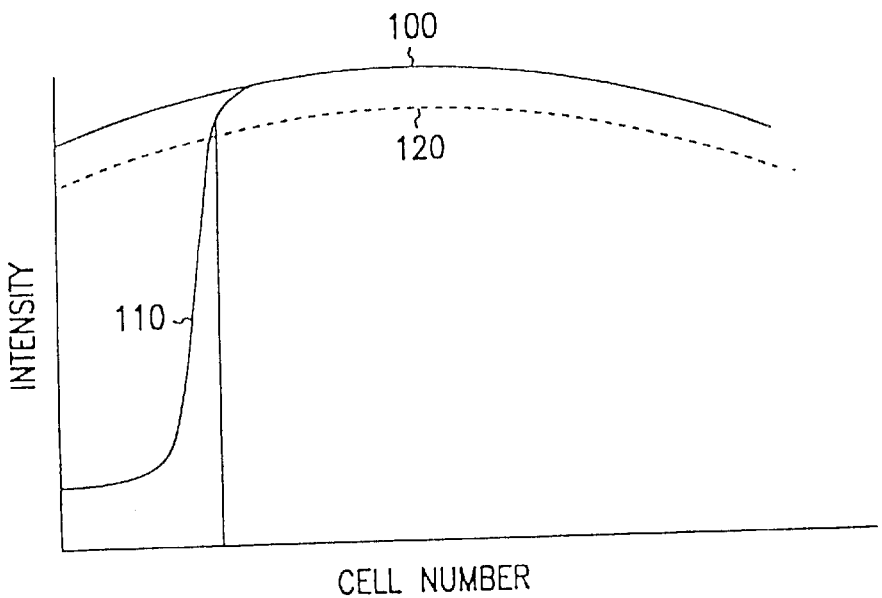
FIG. 5b is a typical graph of illumination intensity as a function of array cell number.
Figure 6:
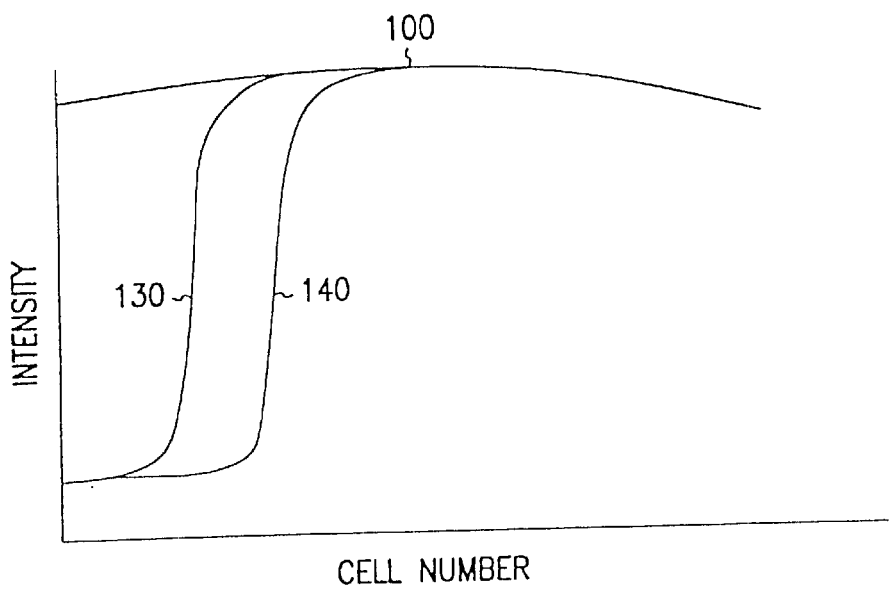
FIG. 6 is a graph illustrating a calibration method of the present invention.

In standard refractometric procedures refractometer 22 is initiated in air with nothing on top of prism 50. In that case all light incident on the interface between the prism and the air is reflected because the prism's index of refraction is usually much higher than that of the air. Therefore, when the refractometer is initiated in air, the sensor detects all the light, and, therefore, there is no shadow line formed on the sensor. Accordingly, the refractometer puts out a reading, which looks like reference curve 100 on FIG. 5 and FIG. 6. Also, under the standard operating conditions, a sample is usually placed on top of the prism with no ligands immobilized on top of the prism. With a sample placed on top of the prism, the critical angle phenomenon is satisfied, and the light incident on the interface becomes partially reflected and partially transmitted, forming the shadow line on the sensor. The refractometer, therefore, produces a reading looking like sample curve 110 in FIG. 5.

Since in the preferred embodiment of the present invention the refractometer is used to sense and monitor interactions between various ligands with transparent disc 78 placed on top of the prism and immobilized binding layer 51' on the disc, initiating the refractometer in air is undesirable. Therefore, in the preferred embodiment of the invention the initialization procedure is performed not in air, but in water. To initialize the refractometer in water, a drop of a coupling liquid, such as oil, was deposited on top of prism 50, then an optically transparent disc was placed on top of the prism. A flow of water was flown over the disc, and the refractometer was allowed to initialize in water, producing the reading such as a water reference curve 130 in FIG. 6. It is noted that it is also possible to initialize the refractometer with the disc on the prism by flowing a low concentration PBS (physiologically buffered saline) over the disc, instead of flowing water. The suitable PBS has a pH of about 7.4 and comprises, for example, 0.14 M NaCI with 0.01 M or 0.1 M phosphate buffer with pH of about 7.4.

If the refractometer was initialized with water or a diluted PBS, as described above, then its calibration procedure can not be performed with water. In that case, a flow of a standard PBS is used to calibrate the instrument, producing a reading, looking like a PBS calibration curve 140 in FIG. 6. Once the refractometer has been initiated and calibrated in accordance with the above-described procedures, it is ready for operation.

During the preparation stage of the experimental trials standard silica glass microscope slides were purchased from Fisher Scientific. Xenobind glass slides were purchased from Xenopore, X, NJ, USA. Xenobind slides are made of silanized glass with a proprietary spacer arm covalently bound to the glass and with an aldehyde group at the terminal end. Biotinylated glass slides were prepared according to the method of Swaisgood et. al, 1997: glass slides were cleaned in 1:4 v/v nitric acid (available from Sigma, St. Louis, Mo., USA) at 95° C. for 1 hour, followed by rinsing with distill water. Slides were then immersed in 10% v/v 3-aminopropyltriethoxysilane—HCl (pH 4.0), incubated at 70° C. for 3 hours and dried at 110° C. overnight, immersed in 5 mg/nI NHS-LC-Biotin (sulfosuccinimidyl 6-(biotinamido) hexanoate (available from Pierce, Rockford, Ill.) in 50 mm sodium bicarbonate (pH 8.5) for 2 hours at 4° C., washed and stored in 50 mm sodium phosphate buffer (pH 6.0) containing 0.02% NaN3. Prior to the start of the experimental trials, slides were cut into 100 mm² square sections. PBS, used in all of the described experimental trials as a control solution for calibration purposes, contained 10 mm of sodium phosphate, 0.138 m of sodium chloride, 2.7 mm of potassium chloride and 0.02% Tween-20. The purpose of the detergent was to minimize non-specific binding.

Each of the Rabbit Anti-Sheep and Goat Anti-Mouse Antibodies was then immobilized on a Xenobind slide as follows: 40 ml of 1 mg/ml antibody was diluted with 400 ml 0.15 M NaCl, 0.1 M Sodium Bicarbonate (pH 9.1). The diluted antibody was spread over the surface of the Xenobind slide. The slides with the immobolized antibodies were then placed in a humidified sealed container overnight in darkness. After that the slides were rinsed with distilled water, dried under a nitrogen stream and immediately used for experimental trials.

For experiments with NeutrAviden conjugated antibodies, the antibody was immobilized on a biotinylated glass slide as follows: 40 ml of 1 mg/ml antibody was diluted with 400 ml of PBS containing 0.02% Tween. Then the diluted antibody was spread onto the slide and allowed to incubate for 3 hours at room temperature in a humidified, sealed, container. The slide was then rinsed with distilled water, dried under a nitrogen stream and immediately used for experimental trials. Alternately, NeutrAviden conjugated antibodies were immobilized on the glass slide by adding them to the mobile phase during the course of the trial.

All experimental trials were conducted according to the following preferred procedure, in which reference is made to the test assembly shown in FIG. 7. A small drop of 1.63 refractive index coupling oil (corresponding to coupling liquid 76 in FIG. 7) was placed on the top of prism 50. The glass slide, corresponding to reference numeral 78 in FIG. 7, was carefully placed on top of the drop of oil to avoid trapping air bubbles between the slide and prism 50. Great care was also taken to be sure the oil did not contact interface 80 with binding layer 51' containing immobilized antibodies (ligands 53 in FIG. 7). The flow cell assembly was completed as described earlier in connection with FIG. 7. PBS containing Tween was then circulated over the slide at 1–2 ml/min for 30 min prior to the start of each experimental trial. The Leica AR600 refractometer was initiated after flowing distilled deionized water over the slide for 3 minutes. Initialization of the refractometer with distilled deionized water provided a reference line of the linear scanned array. The reference line was later used by the software to determine shifts in the shadow line indicative of the critical angle of total reflection. The solution was then switched to PBS with Tween for 5 minutes to calibrate the refractometer. Once calibrated, the refractometer was set to read refractive indices at a series of pre-set intervals. For the experimental trials described below, 124 scans of the linear scanned array were taken for each reading.

Typically, PBS was flown over the slide surface until a stable reference line was achieved. Contacting phase 59, containing the control protein or an antigen. as a sample analyte, was then added to the reservoir (reference numeral 26 in FIG. 3b) and the refractive index of the binding layer 51' was monitored for about 10 to 30 minutes. The control solution was run to distinguish non-specific binding from true antigen/antibody binding interactions. In addition, increasing the antigen concentration in the reservoir provided information about the dependence of the rate of binding interactions on the flow rate and antigen concentration.

Figure 8:
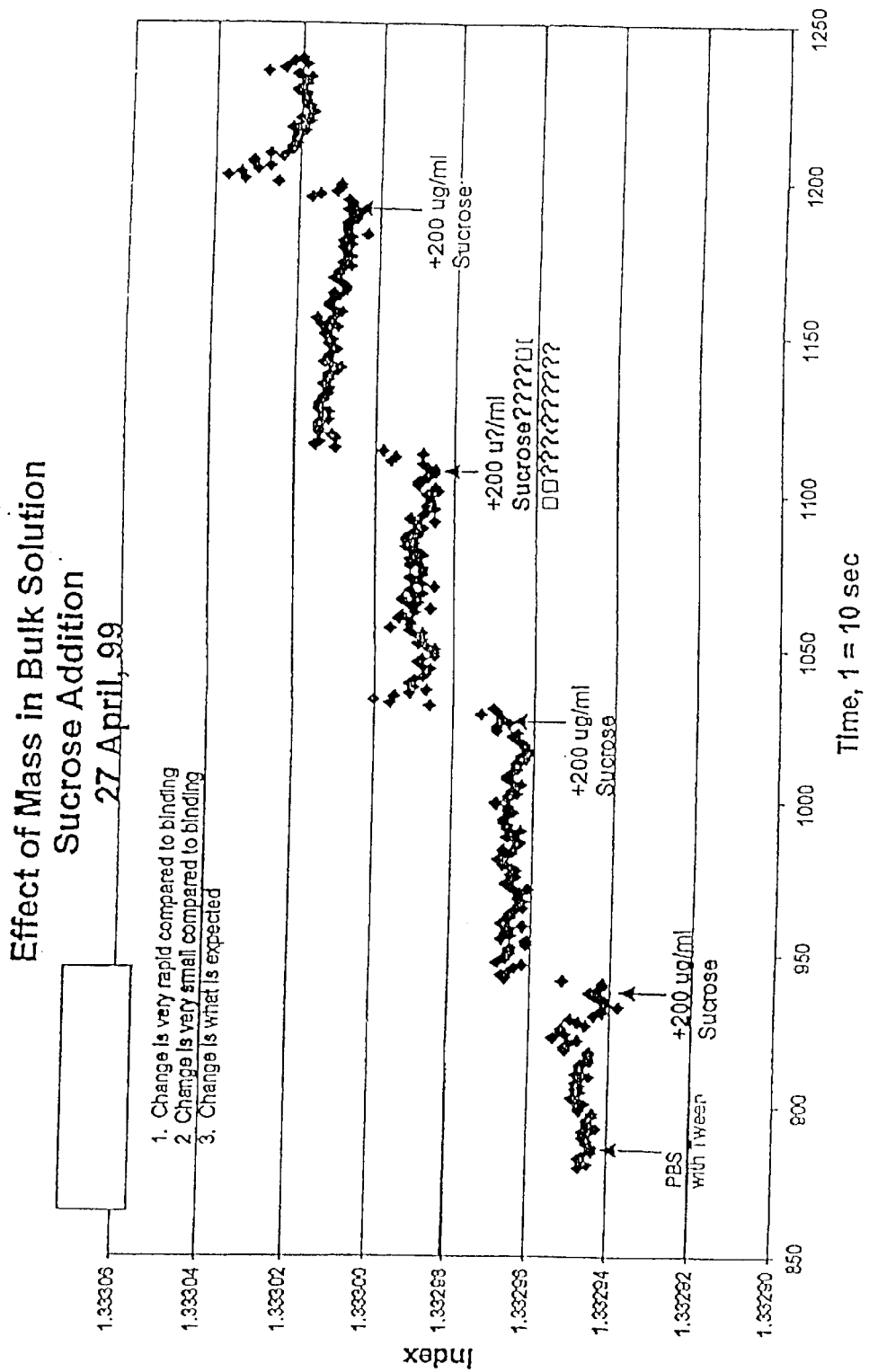
FIG. 8 is a graph illustrating the effect of sucrose addition on the refractive index.

The first experimental trial was conducted to show that a critical angle refractometer with the preferred test assembly, illustrated in FIG. 7, could detect changes in the refractive index of a bulk solution, contacting glass slide 78 with no binding layer 51' on the slide. At the beginning of the experiment, the refractometer was initiated with distilled deionized water and calibrated with PBS, as described above. During the first experimental trial the change in the refractive index was monitored as a function of time for successive additions of sucrose to the recirculating PBS buffer. The observed changes in the refractive index, shown in FIG. 8, were as expected from the well-known relationship between the concentration of sucrose and the refractive index. It was also noted that the changes in the refractive index were immediate, which, again, was an expected observation due to a high flow rate (>1.0 ml/min) of the contacting phase and a low flow cell volume (<30 ml), resulting in minimal dilution effects.

Figure 9:
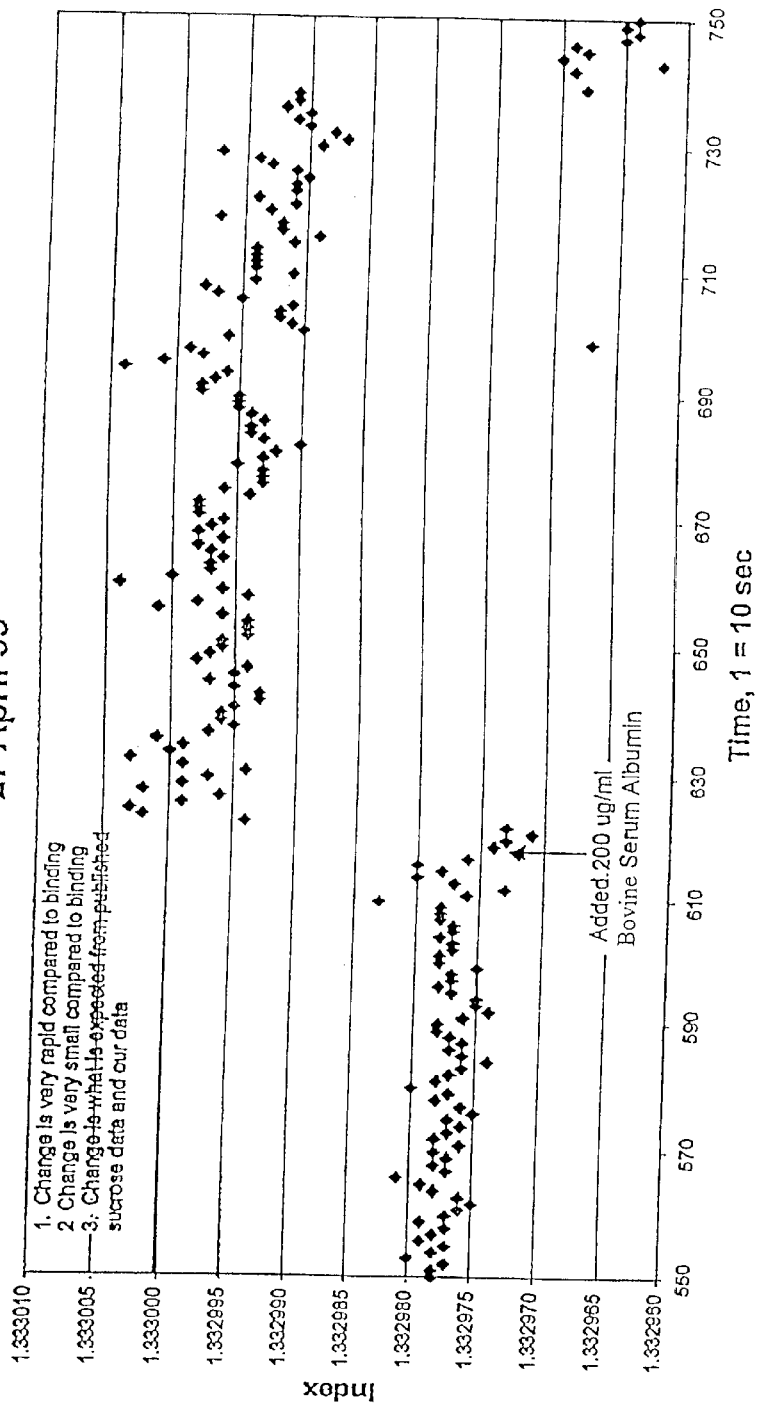
FIG. 9 is a graph illustrating the effect of Bovine Serum Albumin addition on the refractive index.

The second experimental trial was similar to the first one, except that a large mass of added protein Bovine Serum Albumin (BSA) was used to observe the change in the refractive index. Similarly to the first trial, the change in the refractive index, illustrated in FIG. 9, was immediate and of the expected magnitude for the added mass of BSA. The BSA trial also demonstrated the effects of non-specific binding to the binding layer were minimal.

The first and second experimental trials demonstrated that the described configuration of the AR600 refractometer could detect refractive index changes in a contact phase flowing over a glass slide, coupled by a high index oil to the prism of AR600.

The next four experimental trials (third through sixth) were conducted to show that the same configuration of the critical angle refractometer can detect changes in the refractive index at a binding layer, deposited on the slide, in contact with a sample analyte in a contacting phase. In these trials, the ligands in the binding layer were immobilized antibodies, the contacting phase was PBS, the sample analyte was the antigen with specific affinity to the antibodies. A control solution containing PBS with a non-specific antigen or protein, such as BSA, was also used to make sure that the subsequent observed index changes were due to specific antigen/antibody binding interaction, and not due to non-specific antigen/antibody interaction.

Figure 10A:
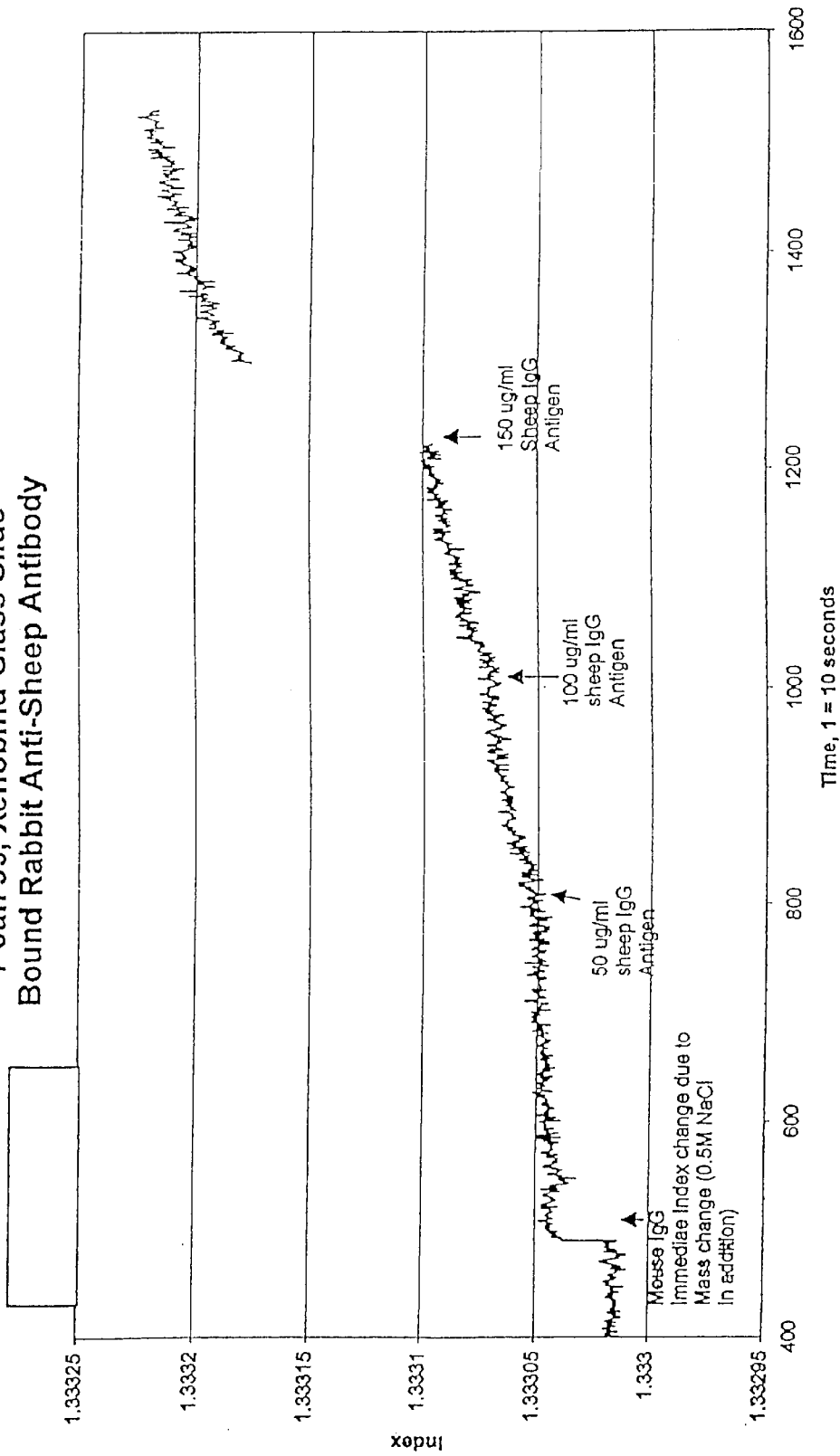
FIG. 10a is a graph illustrating the change in refractive index over time, sensed by measuring the critical angle, the change resulting from binding between Rabbit Anti-Sheep Antibody immobilized on a Xenobind glass slide and Sheep IgG Antigen in the contacting solution.
Figure 10B:
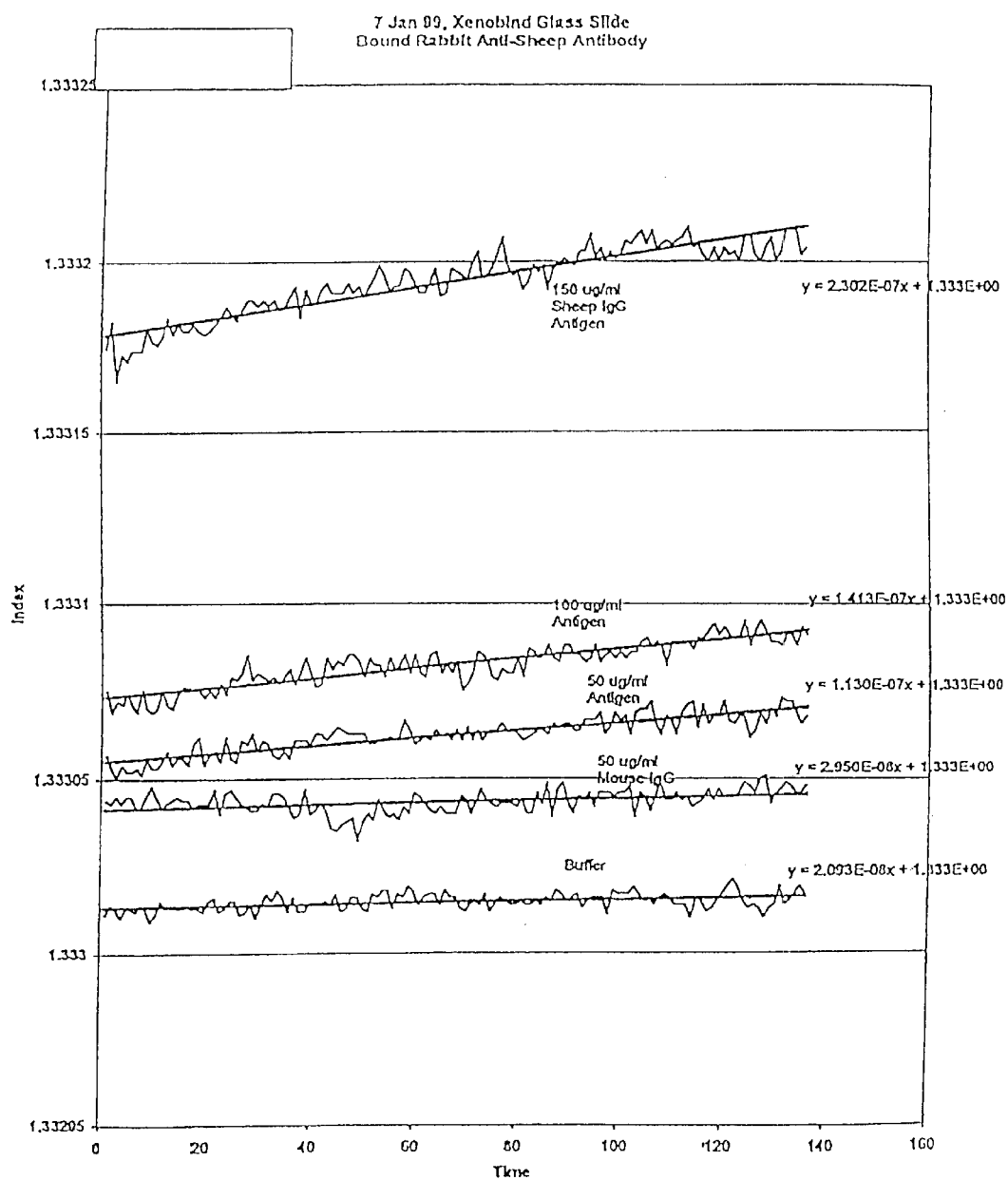

The measurements taken during the third experimental trial, shown in FIG. 10a, represent the refractive index changes at the binding layer of Rabbit Anti-Sheep Antibody immobilized on a Xenobind glass slide. As seen in FIG. 10a, when a stable reference line was established, Mouse IgG was added to the reservoir as a control solution, after which the refractive index was monitored for 45 minutes. Similarly to the observations in the first and second experimental trials, the addition of the non-binding control Mouse IgG solution resulted in the immediate change in the refractive index, due to a high salt concentration in the buffer containing the Mouse IgG. After the immediate change, the refractive index remained almost unchanged for 45 minutes. Subsequent volumes of 50 g/ml Sheep IgG Antigen, having specific affinity to the antibody, were then added to the reservoir every 45 minutes. No immediate jump in the refractive index was observed, due to the fact that the buffer containing the Sheep IgG Antigen was identical to the circulating contacting solution. As can be seen in FIG. 10a, gradual changes in the refractive index were detected each time a quantity of the antigen was added to the contacting phase, which is an indication of the specific binding of the antigen to the immobilized antibody. The data in FIG. 10b, fit by using linear regression, also illustrate that the rate of change in the refractive index increases as the concentration of the antigen increases.

Figure 11A:
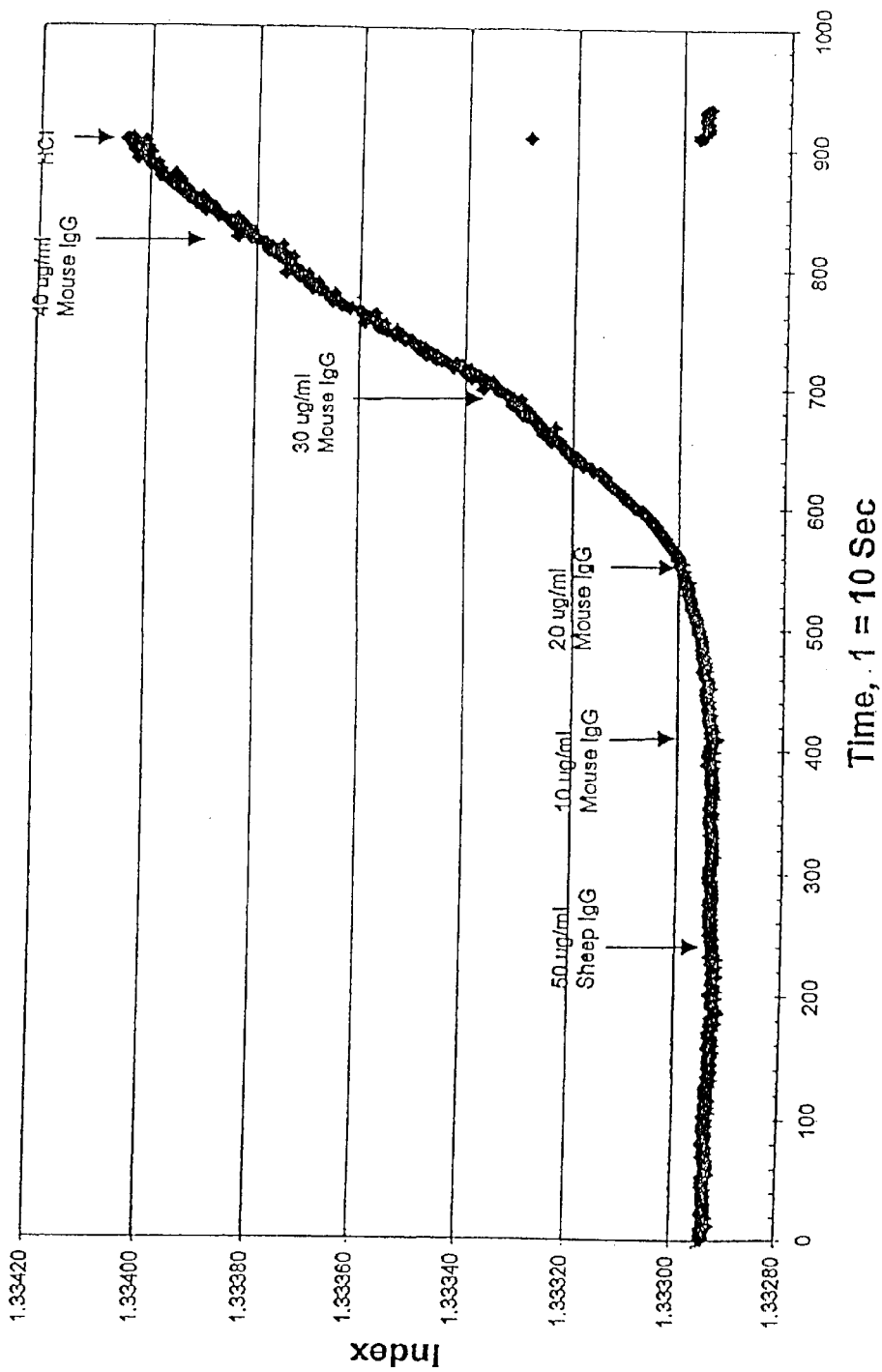
FIG. 11a is a graph illustrating the change in refractive index over time, sensed by measuring the critical angle, the change resulting from binding between Goat Anti-Mouse Antibody immobilized on a Xenobind glass slide and Mouse IgG Antigen in the contacting solution.
Figure 11B:
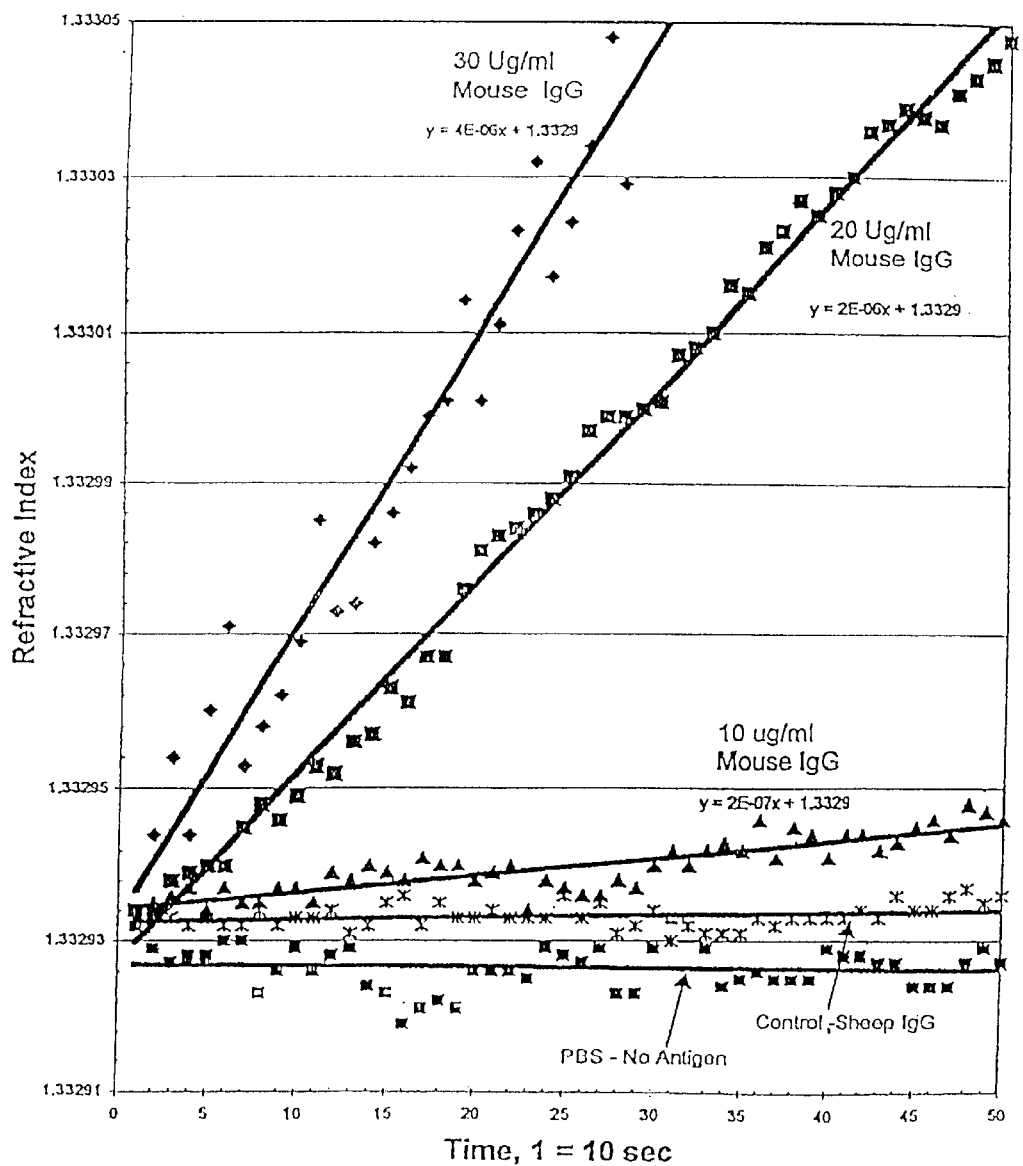

In the fourth experimental trial, Goat Anti-Mouse IgG Antibody was immobilized on a Xenobind slide, as described above. Similarly to the results of the third experimental trial, the refractometer detected changes in the refractive index each time a quantity of antigen was added. As can be seen in FIG. 11a, after the reference line was established, 50 g/ml of non-binding Sheep IgG was added to the reservoir as a control solution. No change in the refractive index was observed with the addition of the non-antigenic non-binding Sheep IgG molecules. Also, no change in the refractive index was observed with large additions of Bovine Serum Albumin (the BSA data are not shown). The Mouse IgG antigen, having specific affinity to the Anti-Mouse IgG antibody, was then added to the reservoir in 10 g/ml increments at approximately 25 minute intervals. As shown in FIG. 11a, the changes in the refractive index were quite large and gradual, as opposed to the immediate changes in the index caused by the mass addition to the contacting phase. Similarly to the data in FIG. 10b, the data in FIG. 11b, fit with linear regression, represent the changes in the refractive index detected by the refractometer during the measurements of the reference line, control solution and antigen additions. As with additions of the Sheep IgG Antigen in the third trial, the rate of change of the refractive index in FIG. 11b increases with the increase of the concentration of the Mouse IgG antigen. Evidently, the gradual increase is caused by binding, and not by the mass addition to the contacting phase. The increase is also of a much greater magnitude than what can be attributed to the mass addition. Therefore, the changes in the index, shown in FIGS. 14a and 14b, were caused by the antigen/antibody binding interactions, detected by the refractometer.

Figure 12:
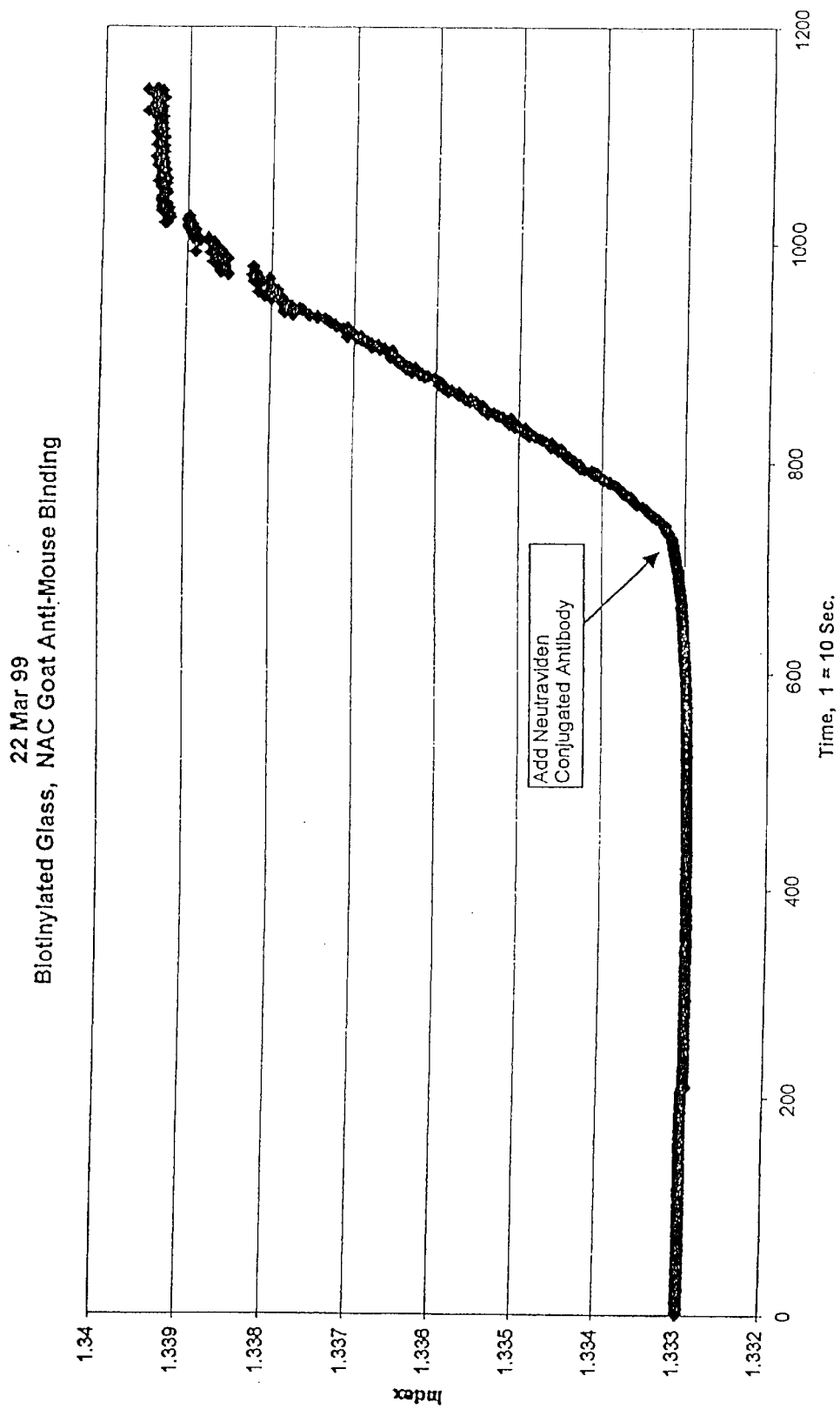
FIG. 12 is a graph illustrating the effect of binding between biotinylated glass and neutraviden conjugated Goat Anti-Mouse Antibody on the refractive index.

The fifth experimental trial was conducted to demonstrate the ability of the refractometer to sense and monitor binding of the NeutrAviden conjugated Goat Anti-Mouse antibody to a biotinylated glass slide. At illustrated in FIG. 12, after the reference line was established, 15 g/ml of the NeutrAviden Conjugated Goat Anti-Mouse Antibody was added to the reservoir. After approximately 40 minutes and an index change of 0.002, the index stopped changing, which is indicative of the saturation of the antigen/antibody binding reaction. Since the index change of 0.001 corresponds to approximately 1 ng/mm² of the immobilized antibody, the total antibody/antigen bound to the surface of the slide is 2 ng/mm² or 200 ng/cm². Such a result is well within the range, expected for these types of experiments.

Figure 13A:
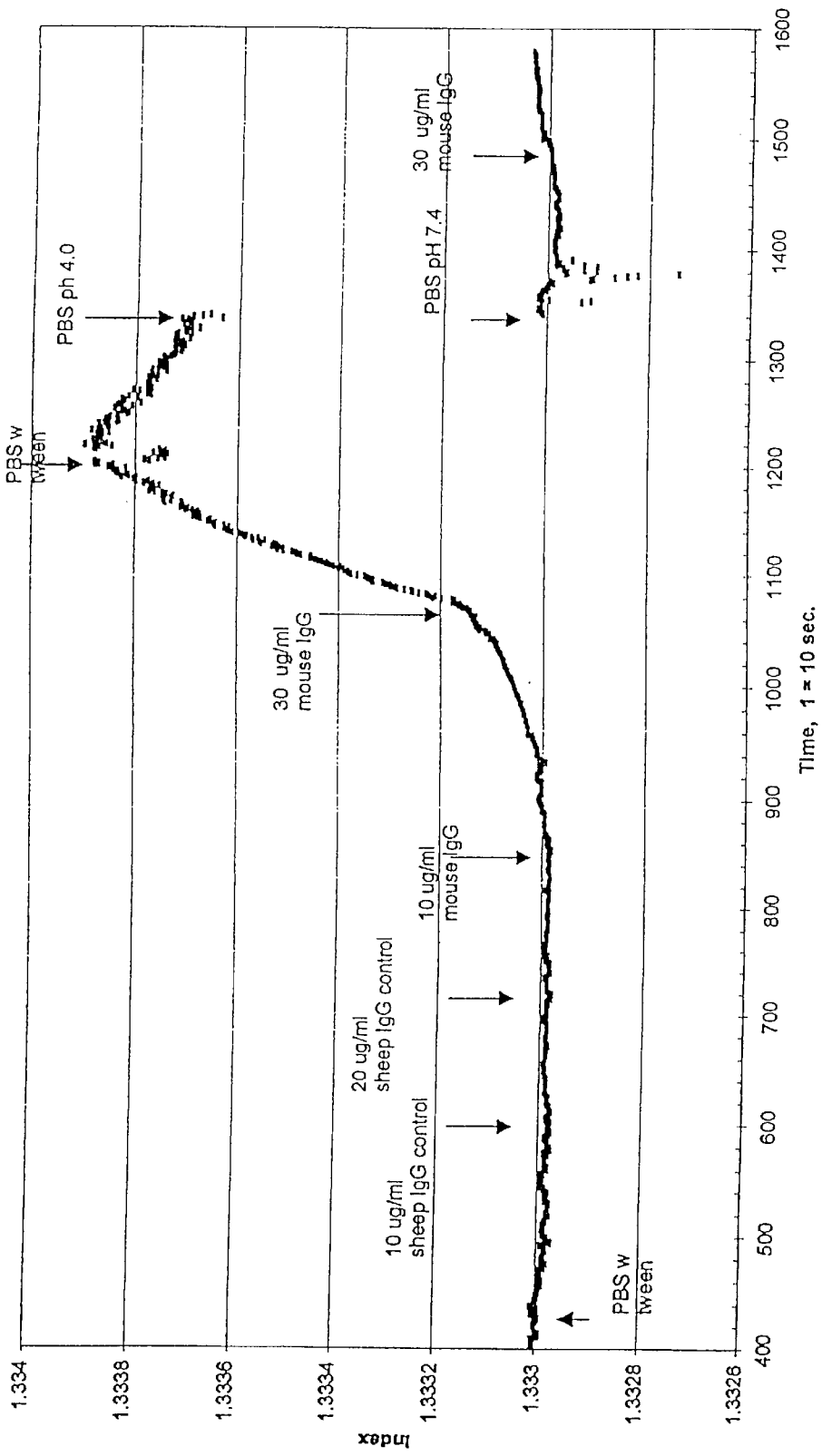
FIG. 13a is a graph illustrating the effect of non-binding and binding ligands on the refractive index.
Figure 13B:
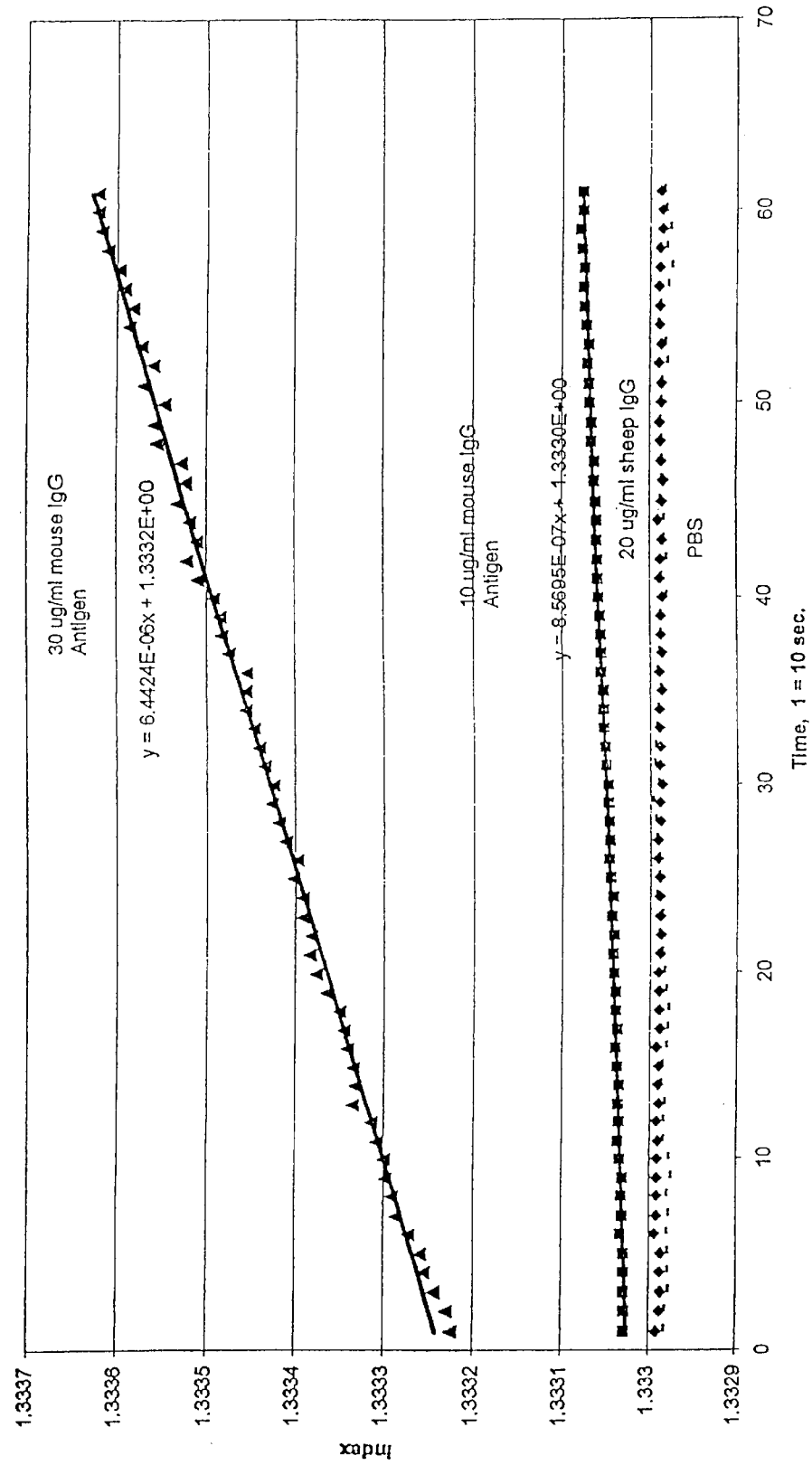

In the sixth experimental trial, the NeutrAviden conjugated Goat-Anti Mouse antibody was immobilized on a biotinylated glass slide. The immobilization step was performed by spreading the diluted antibody solution on the surface of the slide and incubating for 3 hours prior to assembling the slide into the refractometer to prevent non-specific binding of the NeutrAviden conjugated Goat Anti-Mouse antibody to the tubing and the reservoir. (Subsequent experiments with the antigen were much more reproducible, when the entire flow cell arrangement was not pre-exposed to the NeutrAviden conjugated antibody). FIG. 13a illustrates the changes in the refractive index at the binding layer of the NeutrAviden conjugated Goat Anti-Mouse antibody immobilized on the slide during the course of the experimental trial. Similarly to the previous experiments, the PBS reference line was allowed to stabilize and the control non-binding Sheep IgG solution was added in large excess. As can be seen in FIG. 13a, two additions of 10 g/ml of the Sheep IgG control solution did not result on any change of the refractive index. Alternately, a BSA control solution was added. (The BSA data are not shown). The control solutions were circulated to make sure that the subsequent observed index changes were due to specific antigen/antibody binding interaction, and not due to non-specific antigen/antibody interaction. Additions of the Mouse IgG Antigen were then made to the reservoir in the presence of either the IgG or BSA control solution, or a combination of both. 0.02% Tween 20 detergent in the PBS was also present to minimize non-specific binding. As can be seen in FIG. 13a, the presence or absence of the control solutions in the contacting phase had little or no effect on the refractive index. Only when 10 g/ml and then 20 g/ml of the Mouse IgG Antigen were added to the reservoir did the gradual changes in the refractive index occur. Such changes, again, are attributed to the specific antigen/antibody binding, detected and monitored by the refractometer. FIG. 13b provides the fitted data, illustrating the refracting index changes, corresponding to the addition of the control Sheep IgG solution and two additions of the antigen to the reservoir. Again, the observed changes occurred due to the antigen/antibody binding interactions.

Figure 16A:
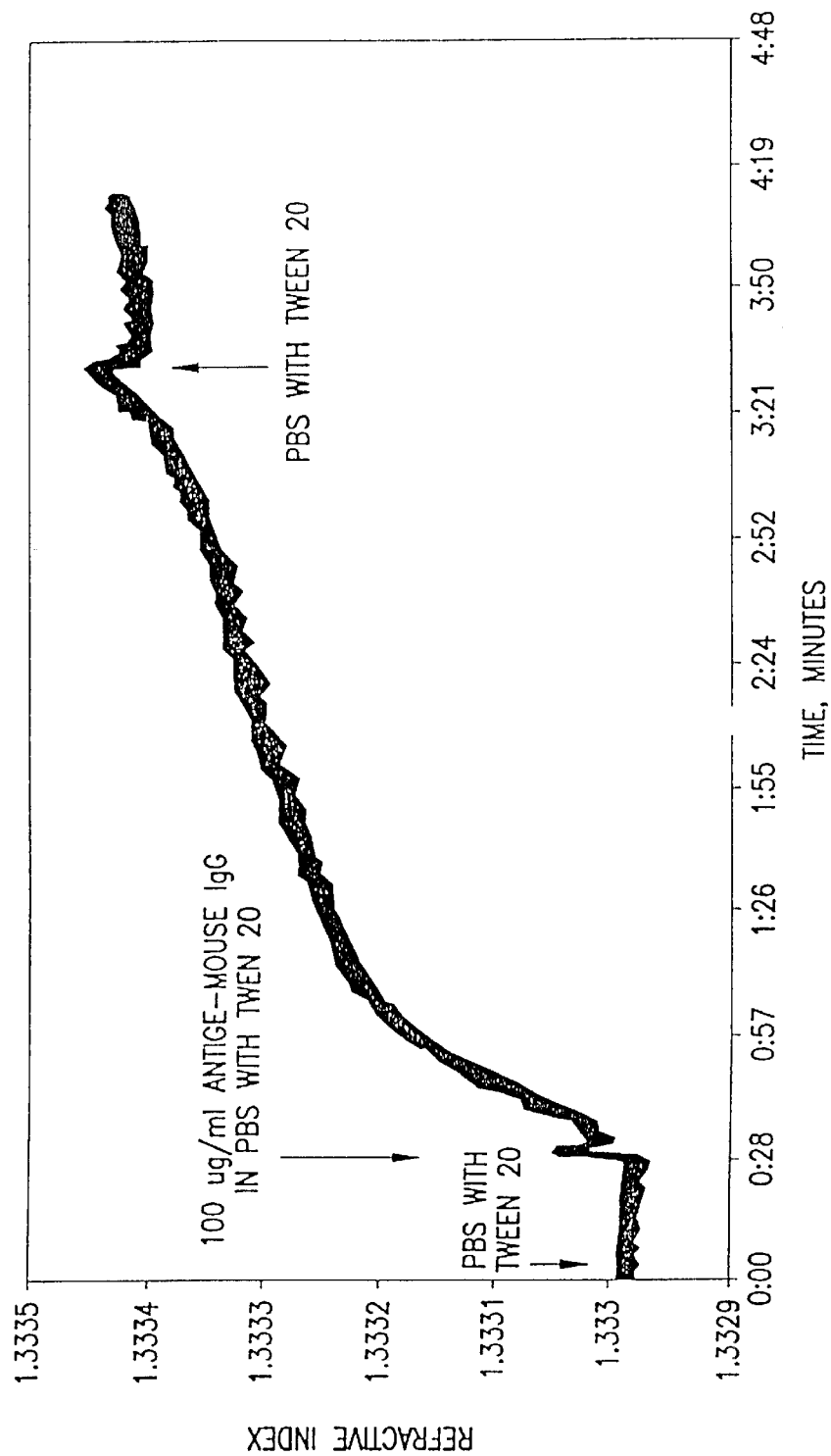
FIG. 16a is a graph illustrating changes in the refractive index over time, sensed by measuring the critical angle, the change resulting from binding between a biotinylated glass slide and Neutraviden conjugated Goat Anti-Mouse IgG Antigen in the contacting solution.
Figure 16B:
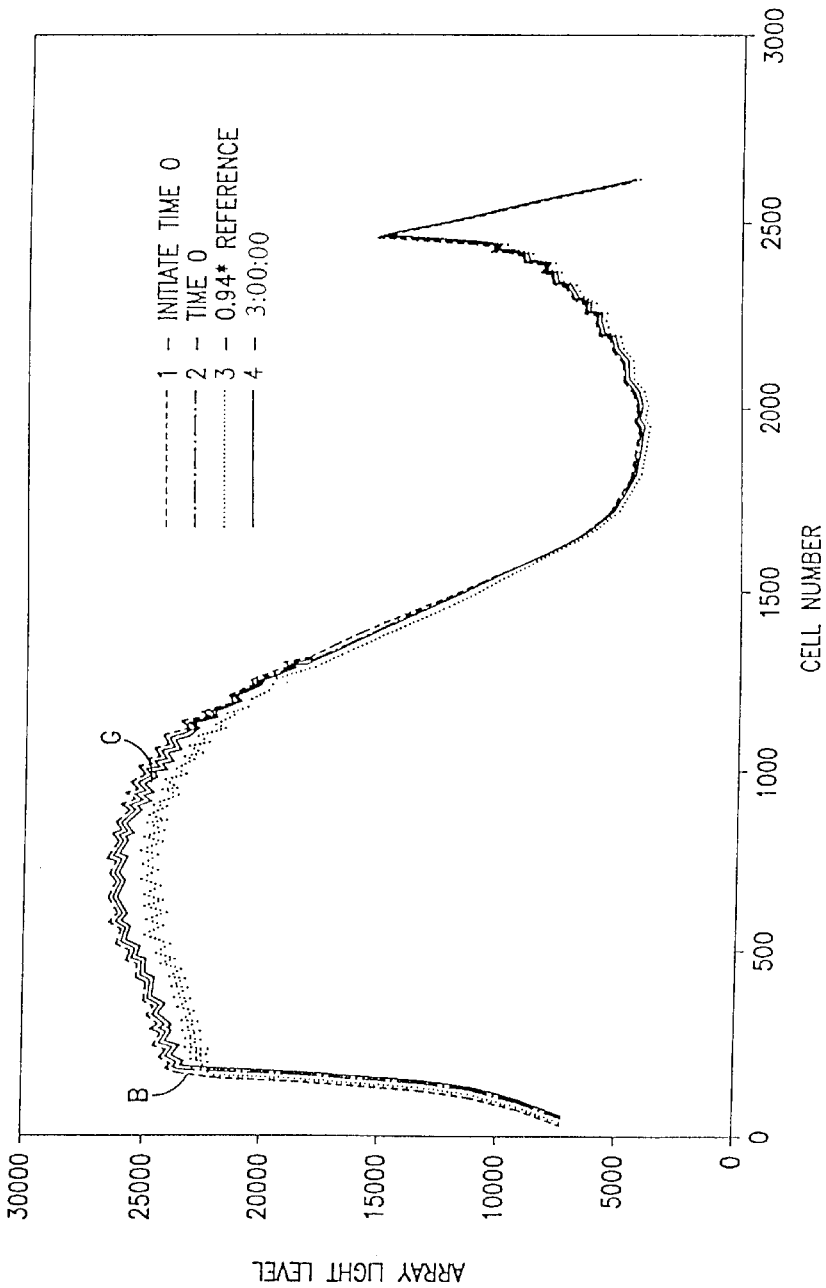
Figure 16C:
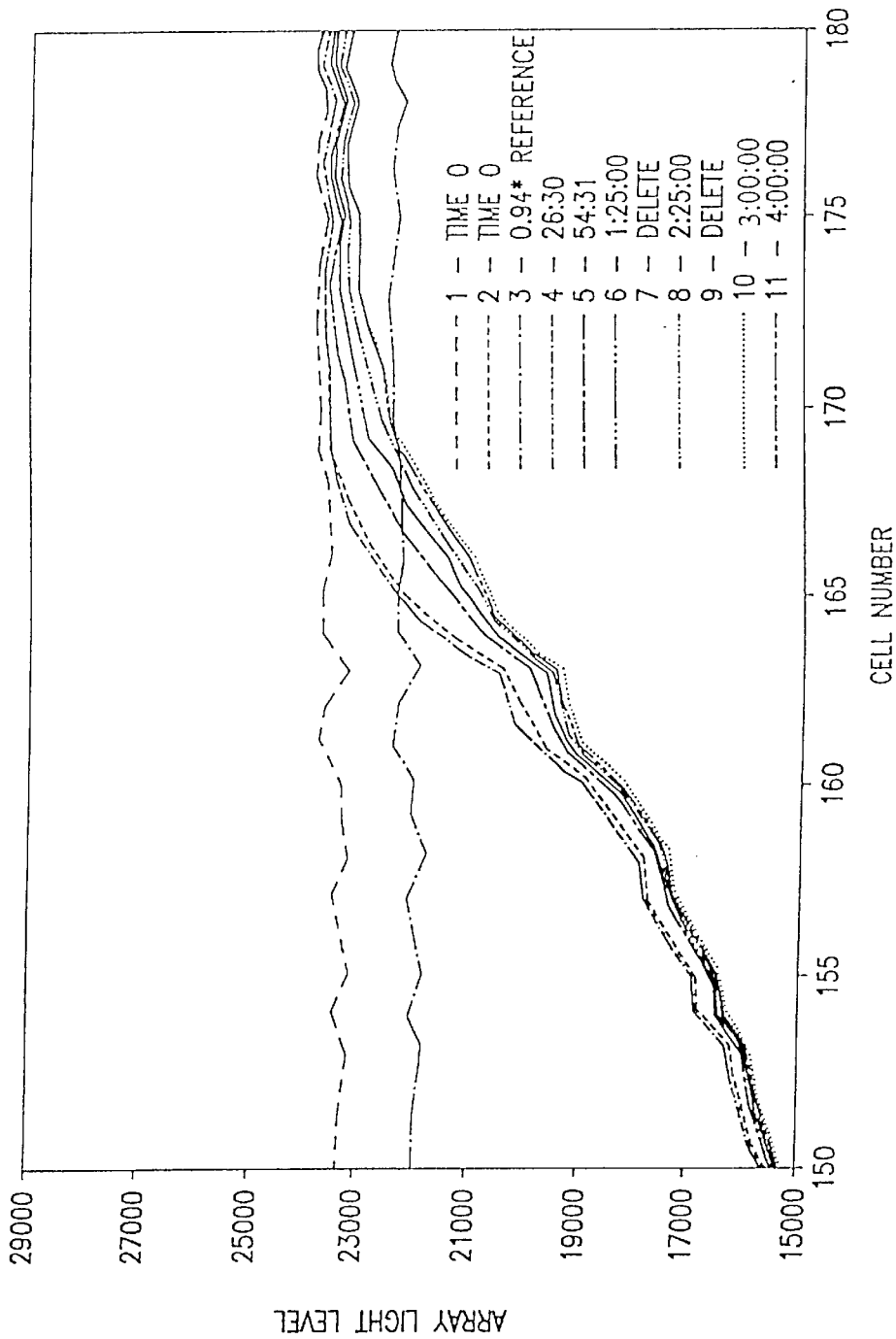

The seventh experimental trial, the results of which are shown in FIGS. 16a–16d, was identical to the sixth trial, except for the fact that 100 g/ml Mouse IgG antigen was added to the solution to elicit a response. FIG. 16a shows changes in the refractive index of the contacting phase after the addition of the antigen. FIG. 16b illustrates intensity changes over the time during which the seventh experimental trial was conducted. It can be seen in FIG. 16b that the position of the shadow line relative to the position of the shadow line during initiation of the instrument ("G" and "B", respectively, in FIG. 16b ). FIG. 16c shows that during the course of the experimental trial not only are there changes in the position of the shadow line in response to the addition of the Mouse IgG, but also there are changes in the intensity of the response. FIG. 16d shows the position of the shadow line at the beginning ("B") and at the end ("G") of the experimental trial. These graphs illustrate how the position of the intensity of the shadow line changes with the addition of the Mouse IgG to the contacting phase and during the binding reaction between the Mouse IgG and the binding layer immobilized on the slide.

The above described experiments demonstrated that critical angle refractometry can be successfully used to detect and monitor binding interactions between a sample analyte and a binding layer by measuring changes in the refractive index at the binding layer. Based on the experimental results, various embodiments of the method and device of the present invention are described below by way of example, and not limitation. It is intended that other embodiments implementing the use of critical angle refractometry for sensing and monitoring binding interactions between various ligands fall within the scope and spirit of the present invention.

Figure 4:
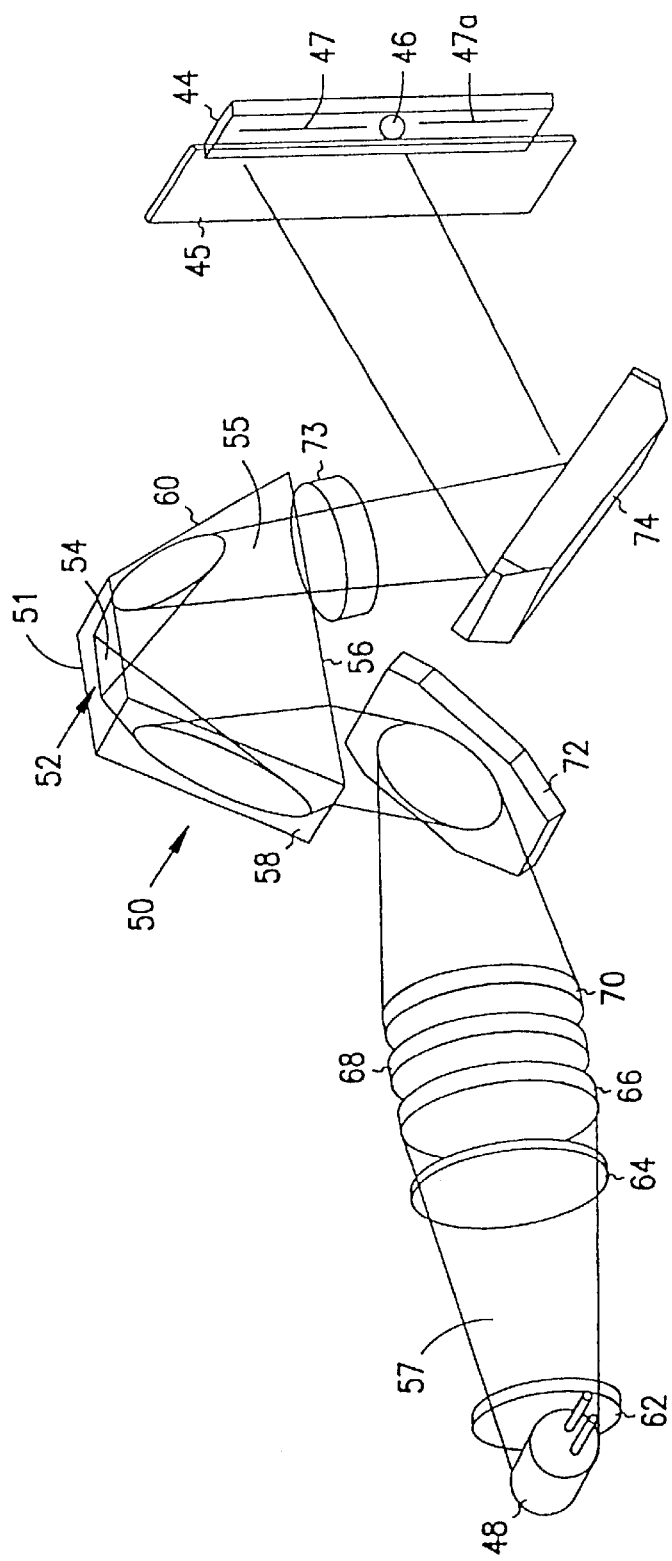

As described above, in the schematic representation of the optical measurement system of automatic refractometer Leica AR600 (FIG. 4) the light from source 48 travels along optical path 57 and illuminates top surface 54 of prism 50 at various angles of incidence. The portion of light, which is incident on surface 54 at the angles greater than the critical angle, is reflected back and sensed by LSA 44. The portion of light incident on surface 54 at the angles smaller than the critical angle is transmitted into sample 51 and escapes the LSA. The same principle can be used to sense binding interactions in a different embodiment of the device, in which light source 48 generates a collimated light beam incident on top surface 54 of prism 50 or any other sensing surface at a predetermined angle of incidence α. If, for example, the binding layer is deposited directly on surface 54 of prism 50, then interface 80 will be the interface between surface 54 and the binding layer. Alternatively, if binding layer 51' is deposited on transparent disc 78, then interface 80 will be the interface between the disc and the binding layer.

Figure 15A:
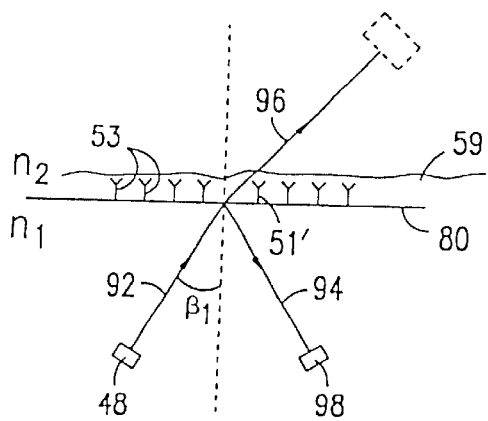
FIG. 15a is a schematic illustration of the optical system of one embodiment of the present invention.

For example, shown schematically in FIG. 15*a* is a light beam 92 generated by light source 48, which light beam 92 is incident on interface 80 at angle $\alpha_1$. The positions of light source 48 and a sensor 98 in the embodiment will be predetermined. If a particular analyte with specific affinity to binding layer 51' is present in contacting phase 59, then the binding will occur, and the refractive index n2 at the binding layer will increase, while n1 remains unchanged. Since n2 increases, then, according to Snell's law the critical angle of total reflection will increase. Since in the described embodiment the angle of incidence $\alpha_1$ is fixed, choosing $\alpha_1$ to be greater than or equal to the critical angle when no analyte is bonded to the binding layer, but smaller than the critical angle when the analyte is bonded to the layer, will cause light beam 92 to be totally reflected at interface 80 with no analyte bonded, but to be transmitted through the contacting phase when the analyte is bonded to the layer. Therefore, when no analyte is bonded, reflected light beam 94 will illuminate sensor 98. Once the analyte binds to the binding layer, sensor 98 will not sense reflected light beam 94. Another sensor (shown in dashed lines in FIG. 15*a*) can be positioned to sense a transmitted light beam 96, if a particular method and design of the embodiment calls for sensing transmitted light. By sensing either the presence of reflected beam 94 with sensor 98 or the presence of transmitted beam 96 with sensor 98 positioned to detect the transmitted beam (depicted by dashed lines in FIG. 15*a*), the presence or absence of binding interactions between the binding layer and the analyte in the contacting phase can be determined. If the embodiment uses one sensor, then the transition between sensing and not sensing light will be indicative of binding. Sensor 98 can be a simple photo sensing device, indicating whether beam 94 (or beam 96) illuminates the sensing device, or an LSA, or any other sensor capable of detecting light. Sensing binding interactions in this embodiment of the invention can be used in devices aimed to detect presence or absence of a particular substance in a sample. An example of such a device is a "yes/no" test device, which is able to indicate whether a particular type of ligands (protein, antigen etc.) is present in the sample. Blood and urine samples, for example, can be analyzed for presence of a particular substance by a user at home or by laboratory personnel in a lab by using the above described test device embodiment.

Figure 15B:
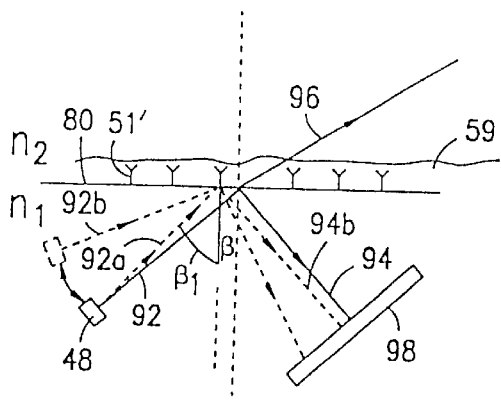
FIG. 15b is a schematic illustration of the optical system of another embodiment of the present invention.

In yet another embodiment of the present invention, depicted in FIG. 15*b*, a single light source 48 is allowed to move, rotationally or translationally (shown by arrows in FIG. 15*b*), changing the trajectory of an incident collimated light beam 92 to become either beam 92*a* or beam 92*b*, thereby altering the angle of incidence of collimated light beam 92 (as depicted by dashed lines in FIG. 15*b*). Similarly to the theory underlying the description of the embodiment in FIG. 15*a*, when binding between the analyte and binding layer 51' occurs, n2 increases, increasing the critical angle of total reflection. If the original angle of incidence was greater than or equal to the critical angle of total reflection when no analyte was bonded to the binding layer, then sensor 98 senses reflected bean 94. When contacting phase 59 contains the analyte reacting with the binding layer, then when binding occurs, the angle of incidence no longer satisfies the condition of total reflection. By moving or rotating source 48, a different angle (such as $\alpha_1$) greater then the critical angle is then selected, so sensor 98 detects reflected beam 94*b*. In that embodiment, the sensor can be an LSA, though it is not necessary. As in the embodiment described with regard to FIG. 15*a*, sensing either reflected beam 94 or transmitted beam 96 can be performed to detect binding. The light source can be an LED.

Figure 15C:
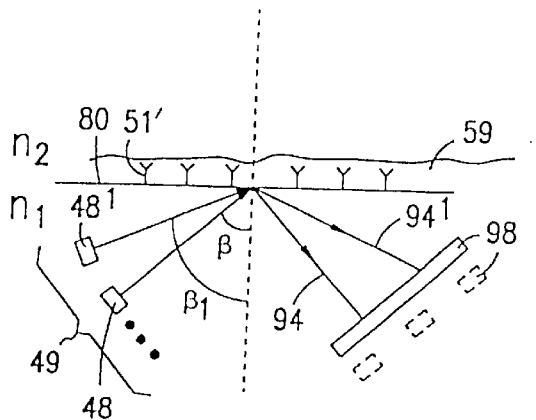
FIG. 15c is a schematic illustration of yet another embodiment of the present invention.

Alternatively, instead of moving or rotating one light source (source 48 in FIG. 15*b*), a plurality of fixed or movable light sources 49 (FIG. 15*c*) can be used to direct light beams at interface 86 at different angles of incidence. When the critical angle increases due to binding between the analyte and binding layer 51', a light beam from a different source 48' can be directed to interface 80 at a greater angle of incidence $\alpha_1$. If $\alpha_1$ is greater than the critical angle of total reflection when the analyte is bonded to the binding layer, then sensor 98 will detect binding by sensing reflected beam 94'. Sensor 98 can comprise one sensor, such as an LSA, or a plurality of sensors, as shown in dashed lines in FIG. 15*c*.

It is also contemplated that when a collimated light beams illuminates interface 80, as described with regard to FIGS. 18*b* and 18*c*, instead of moving or rotating the light source, the incident angle can be altered, and the condition of total internal reflection can be satisfied, by moving or rotating the optically transparent element on which the binding layer was immobilized.

As can be appreciated, the present invention encompasses an apparatus and method for sensing and monitoring binding interactions between various ligands by observing changes in the refractive index over time attributed to binding. The refractive index changes are observed by measuring changes in the critical angle of total reflection at a binding layer using shadow line analysis. Consequently, a non-metallic, optically transparent element is used to immobilized the binding layer, thereby simplifying immobilization procedures considerably. Moreover, relatively low-cost instrumentation may be substituted for much higher cost SPR biosensing devices. Accordingly, the present invention saves both technician time and equipment expense.

It is contemplated to use the present invention for sensing and monitoring a variety of binding interactions, including but not limited to antigen/antibody, drug/receptor, polynucleotide strand/complementary polynucleotide strand, aviden/bioten, immunoglobulin/protein A, enzyme/substrate, and specific carbohydrate/lectins interactions. Measurement output may be in the form of a GO/NO GO report, for example by LCD display 38, as may be useful in testing for the presence of *E. coli*. or other food born pathogens. The present invention could also provide diagnostic information, which is currently obtained by enzyme linked immunosorbant assay (ELISA) and radio-immuno assays. The method and apparatus of the present invention can be implemented in devices of various sizes, ranging from hand held sensors to larger industrial sensor systems. Applications of the method and apparatus of the present invention also include sensing and monitoring of environmental pollutants, pesticides, and metabolites, water quality control, drug discovery, research and manufacture, diagnosing chemical substance abuse, food and beverage processing.

Although specific embodiments have been illustrated and described herein, it will be appreciated by those skilled in the art that any arrangement which is calculated to achieve the same purpose may be substituted for the specific embodiment shown. This application is intended to cover any adaptations or variations of the present invention. Therefore, it is manifestly intended that this invention be limited only by the following claims:

What is claimed is:

1. A method of using critical angle refractometry for sensing presence or absence of an analyte at a binding layer, the method comprising:

providing a first optically transparent element and a second optically transparent element, the first optically transparent element having a higher refractive index than that of the second optically transparent element, the second element having the binding layer;

providing a contacting phase;

allowing the contacting phase to contact the binding layer of the second optically transparent element;

passing light through the first and the second optically transparent elements to cause the light to impinge upon an interface between the second optically transparent element and the binding layer; and detecting a location of a boundary between a light area and a dark area on a sensing element, the location of the boundary being indicative of the presence or absence of the ligands at the binding layer.

2. The method of claim 1 further comprising providing a test assembly designed to house the second optically transparent element and the contacting phase contacting the binding layer, the test assembly being disposed to allow the light to impinge upon the interface between the second optically transparent material and the binding layer.

3. A method of using critical angle refractometry for sensing presence or absence of an analyte at a binding layer of a first optically transparent material, the method comprising:

providing the first optically transparent material of a higher optical density than that of the binding layer;

contacting the binding layer with a contacting phase;

passing light along an optical path through the first optically transparent material to cause the light to impinge upon an interface between the binding layer and the first optically transparent material;

sensing a boundary between a light area and a dark area on a sensing element disposed along the optical path; and utilizing the location of the boundary to determine the presence or absence of the analyte at the binding layer.

4. The method of claim 3, wherein the light area is formed by a first portion of the light reflected from the interface and illuminating the sensing element, the dark area is formed as a result of a second portion of the light transmitted into the contacting phase and not illuminating the sensing element.

5. The method of claim 3, further comprising passing light through a second optically transparent material before passing light through the first optically transparent material.

6. A method of sensing presence or absence of an analyte at a binding layer, the method comprising:

providing an interface between the binding layer and an optically transparent element, the interface being located along an optical path, the binding layer and the optically transparent element having different optical densities sufficient to totally internally reflect light impinging on the interface;

contacting the binding layer with a contacting phase;

illuminating the interface with the light propagating along the optical path, so that a portion of the light totally internally reflected from the interface propagates between the interface and a sensing element disposed along the optical path and illuminates the sensing element to form a light area thereon; and detecting a location of a boundary between the light area and a dark area on the sensing element, the location of the boundary being indicative of the presence or absence of the analyte at the binding layer.

7. The method of claim 6, further comprising passing the light through the optically transparent element before illuminating the interface.

8. The method of claim 7, further comprising passing the light through an optically transparent material before passing the light through the optically transparent element.

9. The method of claim 6, wherein the analyte changes the optical density of the binding layer by binding to immobilized ligands in the binding layer.

10. A method of sensing presence or absence of an analyte at a binding layer, the method comprising:

providing a first interface between a first medium and a second medium, a second interface between the second medium and a third medium, and a third interface between the third medium and the binding layer, the first, the second, the third media and the binding layer having optical densities sufficient to cause light propagating through the first, the second and the third interfaces to be totally internally reflected at the third interface and to propagate toward a sensor;

contacting the binding layer with a contacting phase;

passing the light through the first interface and the second interfaces to cause the light to impinge upon the third interface; and detecting a location of a boundary between a dark area and a light area on the sensor, the location of the boundary being indicative of the presence or absence of the ligands at the binding layer.

11. The method of claim 10, wherein providing the first, the second and the third interfaces comprises providing the first medium, the second medium, the third medium and the binding layer having the optical densities in a descending order from the first medium to the binding layer.

12. A method of sensing presence or absence of an analyte at a binding layer, the method comprising:

providing a light beam generated by a light source;

providing an interface between the binding layer and an optically transparent element, the binding layer and the optically transparent element having optical densities sufficient to cause the light beam impinging upon the interface to be totally internally reflected;

contacting the binding layer with a contacting phase;

illuminating the interface by the light beam impinging upon the interface at a predetermined angle of incidence;

providing a sensor located at a position in which the sensor can sense the light totally internally reflected at the interface; and sensing the presence or absence of a boundary between a dark area and a light area on the sensor, the presence or absence of the boundary being indicative of the presence or absence of the analyte at the binding layer.

13. The method of claim 12, further comprising passing the light beam through the optically transparent element before illuminating the interface.

14. The method of claim 12, further comprising altering the predetermined angle of incidence to allow the sensor to detect a change between sensing light and not sensing light.

15. A method of sensing an analyte at a binding layer, the method comprising:

provide an optically transparent element having an optical density different from that of the binding layer, the optically transparent element comprising the interface between the binding layer and the optically, transparent element;

providing a light source generating a collimated light beam propagating along an optical path, the optical path comprising the light source, the interface and a sensing element;

contacting the binding layer with a contacting phase;

directing the light beam to the interface to cause the light beam to impinge upon the interface at a predetermined angle of incidence; and sensing presence or absence of a boundary between a dark area and a light area on the sensing element to determine the absence of the analyte in the contacting phase.

16. A method of using critical angle refractometry for determining presence or absence of an analyte at a binding layer deposited on an optically transparent element, the method comprising:

providing a critical angle refractometer defining an optical path; the critical angle refractometer comprising a sensing element disposed along the optical path;

directing light along the optical path at an interface between the binding layer and the optically transparent element;

bringing the analyte in contact with the binding layer; and refractometrically detecting changes in an optical density of the binding layer by sensing the light on the sensing element; and and relating the changes to the presence or absence of the analyte at the binding layer.

17. The method of claim 16, further comprising repeating refractometrically detecting changes in the optical density of the binding layer to monitor the interaction between the analyte and the binding layer over time.

18. The method of claim 16, wherein bringing the analyte in contact with the binding layer comprises contacting the binding layer with a contacting phase containing the analyte.

19. The method of claim 16, wherein the changes in the optical density are caused by interaction between the analyte and the binding layer.

20. An apparatus for using critical angle refractometry to sense presence or absence of an analyte at a binding layer, the analyte having affinity to the binding layer, the apparatus comprising:

a first optically transparent element and a second optically transparent element, the first optically transparent element having a higher refractive index than that of the second optically transparent element;

the binding layer deposited on the second optically transparent element, the binding layer having a refractive index lower than that of the second optically transparent element;

a contacting phase contacting the binding layer;

a light beam passing through the first and the second optically transparent elements, causing the light to impinge upon an interface between the second optically transparent element and the binding layer; and a sensor detecting a location of a boundary between a light area and a dark area on the sensor.

21. The apparatus of claim 20, wherein the contacting phase contains the analyte interacting with the binding layer.

22. The apparatus of claim 20, wherein the light area being formed by a portion of the light beam reflected from the interface toward the sensor, the dark area being formed by light refracted into the binding layer.

23. The apparatus of claim 20, further comprising an optically transparent layer disposed between the first optically transparent element and the second optically transparent element.

24. A system for determining presence or absence of an analyte in a contacting phase, the system comprising:

a critical angle refractometer defining an optical path of a light beam impinging upon an interface between an optically transparent element and a binding layer, the binding layer being deposited on the optically transparent element and having affinity to the analyte;

the contacting phase contacting the binding layer; and a sensor sensing a boundary between light and dark areas on the sensor.

25. The system of claim 24, further comprising a test assembly designed to house the optically transparent element.

26. The system of claim 25, wherein the test assembly comprises means for bringing the contacting phase in contact with the binding layer.

27. The system of claim 24, wherein the contacting phase contains the analyte interacting with the binding layer.

28. A system for detecting presence or absence of an analyte in a contacting phase, the system comprising:

an optically transparent element having a binding layer deposited thereon, the binding layer having affinity to the analyte;

a critical angle refractometer defining an optical path of a collimated light beam impinging upon an interface between the binding layer and the optically transparent element;

the contacting phase contacting the binding layer; and a sensor disposed along the optical path to detect changes in an optical density of the binding layer by sensing the collimated light beam travelling along the optical path.

29. The system of claim 28, wherein the critical angle refractometer comprises an optically transparent material disposed along the optical path in such a way that the light beam passes through the material before impinging upon the interface between the binding layer and the optically transparent element.

30. The system of claim 28, wherein the light beam impinges upon the interface at a predetermined angle of incidence.

* * * * *

UNITED STATES PATENT AND TRADEMARK OFFICE
CERTIFICATE OF CORRECTION

PATENT NO. : 6,462,809 B1
DATED : October 8, 2002
INVENTOR(S) : Ryan et al.

It is certified that error appears in the above-identified patent and that said Letters Patent is hereby corrected as shown below:

<u>Title page,</u>
Item [75], Inventors, should read -- Thomas E. Ryan, Batavia; Michael J. Byrne, East Aurora, Robert C. Atkinson, Buffalo, all of NY (US) --

Signed and Sealed this

Eighteenth Day of March, 2003

JAMES E. ROGAN
*Director of the United States Patent and Trademark Office*